US011453626B2

(12) United States Patent
Fan et al.

(10) Patent No.: US 11,453,626 B2
(45) Date of Patent: Sep. 27, 2022

(54) ALKENE GENERATION USING METAL SULFIDE PARTICLES

(71) Applicant: OHIO STATE INNOVATION FOUNDATION, Columbus, OH (US)

(72) Inventors: Liang-Shih Fan, Columbus, OH (US); Deven Baser, Columbus, OH (US); Sourabh Nadgouda, Columbus, OH (US); Anuj Joshi, Columbus, OH (US); Pinak Mohapatra, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 0 days.

(21) Appl. No.: 17/602,889

(22) PCT Filed: Apr. 8, 2020

(86) PCT No.: PCT/US2020/027324
§ 371 (c)(1),
(2) Date: Oct. 11, 2021

(87) PCT Pub. No.: WO2020/210396
PCT Pub. Date: Oct. 15, 2020

(65) Prior Publication Data
US 2022/0089511 A1 Mar. 24, 2022

Related U.S. Application Data

(60) Provisional application No. 62/831,617, filed on Apr. 9, 2019.

(51) Int. Cl.
*C07C 5/46* (2006.01)
*C07C 5/48* (2006.01)

(52) U.S. Cl.
CPC . *C07C 5/46* (2013.01); *C07C 5/48* (2013.01)

(58) Field of Classification Search
CPC .................................. C07C 5/46; C07C 5/48
See application file for complete search history.

(56) References Cited

U.S. PATENT DOCUMENTS

| 971,206 A | 9/1910 | Messerschmitt |
| 1,078,686 A | 11/1913 | Lane |
| (Continued) | | |

FOREIGN PATENT DOCUMENTS

| CN | 1329761 A | 1/2001 |
| CN | 1325319 A | 12/2001 |
| (Continued) | | |

OTHER PUBLICATIONS

International Search Report and Written Opinion for Application No. PCT/US2020/027324 dated Jul. 9, 2020 (10 pages).

(Continued)

*Primary Examiner* — Thuan D Dang
(74) *Attorney, Agent, or Firm* — Michael Best & Friedrich LLP

(57) ABSTRACT

Systems and methods include providing a gaseous alkane input stream and metal sulfide (MSx) particles that can react with an alkane in the gaseous alkane input stream to generate an alkene, a reduced metal sulfide (MSx-1) particle, and at least one of: hydrogen sulfide (H2S) and at least one sulfur containing compound selected from: S2, CS, and CS2. A product stream can be collected that includes the alkene and at least one of: hydrogen sulfide (H2S) and the at least one sulfur containing compound. A reduced metal sulfide (MSx-1) particle reacts with sulfur in a sulfur stream and can generate the metal sulfide (MSx) particle and hydrogen (H2).

20 Claims, 20 Drawing Sheets

(56) References Cited

U.S. PATENT DOCUMENTS

| | | |
|---|---|---|
| 1,658,939 A | 2/1928 | Parsons |
| 2,182,747 A | 12/1939 | Marshall, Jr. |
| 2,198,560 A | 4/1940 | Marshall, Jr. |
| 2,449,635 A | 9/1948 | Barr |
| 2,614,067 A | 10/1952 | Reed et al. |
| 2,635,947 A | 4/1953 | Reed et al. |
| 2,686,819 A | 8/1954 | Johnson |
| 2,694,622 A | 11/1954 | Reed et al. |
| 2,697,686 A | 12/1954 | Leffer |
| 2,899,374 A | 8/1959 | Gomory |
| 2,979,384 A | 4/1961 | Weiner et al. |
| 3,027,238 A | 3/1962 | Watkins |
| 3,031,287 A | 4/1962 | Benson et al. |
| 3,338,667 A | 8/1967 | Pundsack |
| 3,353,925 A | 11/1967 | Baumann et al. |
| 3,382,033 A | 5/1968 | Kitagawa |
| 3,421,869 A | 1/1969 | Benson |
| 3,442,613 A | 5/1969 | Grotz, Jr. |
| 3,442,619 A | 5/1969 | Huebier et al. |
| 3,442,620 A | 5/1969 | Huebier et al. |
| 3,494,858 A | 2/1970 | Luckenbach |
| 3,523,821 A | 8/1970 | Bryce et al. |
| 3,573,224 A | 3/1971 | Strelzoff et al. |
| 3,619,142 A | 11/1971 | Johnson et al. |
| 3,726,966 A | 4/1973 | Johnston |
| 3,801,661 A | 4/1974 | Hart et al. |
| 3,879,514 A | 4/1975 | Dahl |
| 3,962,409 A | 6/1976 | Kotera et al. |
| 4,017,270 A | 4/1977 | Funk et al. |
| 4,057,402 A | 11/1977 | Patel et al. |
| 4,075,079 A | 2/1978 | Lang |
| 4,108,732 A | 8/1978 | Nuttall, Jr. |
| 4,151,124 A | 4/1979 | Gidaspow et al. |
| 4,155,832 A | 5/1979 | Cox et al. |
| 4,272,399 A | 6/1981 | Davis et al. |
| 4,318,711 A | 3/1982 | Smith |
| 4,325,833 A | 4/1982 | Scott |
| 4,334,959 A | 6/1982 | Green |
| 4,343,624 A | 8/1982 | Belke et al. |
| 4,348,487 A | 9/1982 | Goldstein et al. |
| 4,404,086 A | 9/1983 | Oltrogge |
| 4,420,332 A | 12/1983 | Mori et al. |
| 4,439,412 A | 3/1984 | Behie et al. |
| 4,521,117 A | 6/1985 | Ouwerkerk et al. |
| 4,594,140 A | 6/1986 | Cheng |
| 4,778,585 A | 10/1988 | Graff |
| 4,842,777 A | 6/1989 | Lamort |
| 4,861,165 A | 8/1989 | Fredriksson et al. |
| 4,869,207 A | 9/1989 | Engstrom et al. |
| 4,902,586 A | 2/1990 | Wertheim |
| 4,895,821 A | 6/1990 | Kainer et al. |
| 4,957,523 A | 9/1990 | Zarate et al. |
| 5,130,106 A | 7/1992 | Koves et al. |
| 5,365,560 A | 11/1994 | Tam |
| 5,447,024 A | 9/1995 | Ishida et al. |
| 5,456,807 A | 10/1995 | Wachsman |
| 5,509,362 A | 4/1996 | Lyon |
| 5,518,187 A | 5/1996 | Bruno et al. |
| 5,529,599 A | 6/1996 | Calderon |
| 5,584,615 A | 12/1996 | Micklich |
| 5,630,368 A | 5/1997 | Wagoner |
| 5,730,763 A | 3/1998 | Manulescu et al. |
| 5,770,310 A | 6/1998 | Nogochi et al. |
| 5,827,496 A | 10/1998 | Lyon |
| 5,858,210 A | 1/1999 | Richardson |
| 5,891,415 A | 4/1999 | Alkhazov et al. |
| 5,965,098 A | 10/1999 | Boegner et al. |
| 6,007,699 A | 12/1999 | Cole |
| 6,030,589 A | 2/2000 | Hartweg et al. |
| 6,143,203 A | 11/2000 | Zeng et al. |
| 6,143,253 A | 11/2000 | Radcliffe et al. |
| 6,180,354 B1 | 1/2001 | Singh et al. |
| 6,187,465 B1 | 2/2001 | Galloway |
| 6,361,757 B1 | 3/2002 | Shikada et al. |
| 6,395,944 B1 | 5/2002 | Griffiths |
| 6,412,559 B1 | 7/2002 | Gunter et al. |
| 6,444,712 B1 | 9/2002 | Janda |
| 6,494,153 B1 | 12/2002 | Lyon |
| 6,506,351 B1 | 1/2003 | Jain et al. |
| 6,509,000 B1 | 1/2003 | Choudhary et al. |
| 6,517,631 B1 | 2/2003 | Bland |
| 6,607,704 B2 | 8/2003 | Guttridge et al. |
| 6,631,698 B1 | 10/2003 | Hyppanen et al. |
| 6,642,174 B2 | 11/2003 | Gaffney et al. |
| 6,663,681 B2 | 12/2003 | Kinding et al. |
| 6,667,022 B2 | 12/2003 | Cole |
| 6,669,917 B2 | 12/2003 | Lyon |
| 6,682,714 B2 | 1/2004 | Kindig et al. |
| 6,685,754 B2 | 2/2004 | Kindig et al. |
| 6,703,343 B2 | 3/2004 | Park |
| 6,797,253 B2 | 9/2004 | Lyon |
| 6,834,623 B2 | 12/2004 | Cheng |
| 6,875,411 B2 | 4/2005 | Sanfilippo et al. |
| 6,880,635 B2 | 4/2005 | Vinegar et al. |
| 6,936,363 B2 | 8/2005 | Kordesch et al. |
| 7,001,579 B2 | 2/2006 | Metzger et al. |
| 7,067,456 B2 | 2/2006 | Fan et al. |
| 7,244,399 B2 | 7/2007 | Myohanen et al. |
| 7,404,942 B2 | 7/2008 | Sanfilippo et al. |
| 7,496,450 B2 | 2/2009 | Aleman et al. |
| 7,749,626 B2 | 7/2010 | Take |
| 7,767,191 B2 | 8/2010 | Thomas et al. |
| 7,837,975 B2 | 11/2010 | Iyer et al. |
| 7,840,053 B2 | 11/2010 | Liao |
| 8,116,430 B1 | 2/2012 | Shapiro et al. |
| 8,192,706 B2 | 6/2012 | Grochowski |
| 8,202,349 B2 | 6/2012 | Molaison |
| 8,419,813 B2 | 4/2013 | Hoteit et al. |
| 8,435,920 B2 | 5/2013 | White et al. |
| 8,508,238 B2 | 8/2013 | Mahalingam et al. |
| 8,562,928 B2 | 10/2013 | Gupta |
| 8,761,943 B2 | 6/2014 | Lou et al. |
| 8,771,549 B2 | 7/2014 | Gauthier et al. |
| 8,814,963 B2 | 8/2014 | Apanel et al. |
| 8,877,147 B2 | 11/2014 | Fan et al. |
| 8,877,150 B1 | 11/2014 | Fan et al. |
| 9,017,627 B2 | 4/2015 | Gupta |
| 9,290,386 B2 | 3/2016 | Wasas |
| 9,376,318 B2 | 6/2016 | Fan et al. |
| 9,382,359 B2 | 7/2016 | Kanellopoulos et al. |
| 9,518,236 B2 | 12/2016 | Fan et al. |
| 9,573,118 B2 | 2/2017 | Colozzi et al. |
| 9,616,403 B2 | 4/2017 | Fan et al. |
| 9,777,920 B2 | 10/2017 | Fan et al. |
| 9,790,605 B2 | 10/2017 | Sheehan et al. |
| 9,903,584 B2 | 2/2018 | Fan et al. |
| 10,010,847 B2 | 7/2018 | Fan et al. |
| 10,081,772 B2 | 9/2018 | Fan et al. |
| 2001/0055559 A1 | 12/2001 | Sanfilippo et al. |
| 2002/0011428 A1 | 1/2002 | Scheuerman |
| 2002/0059864 A1 | 5/2002 | Janssen et al. |
| 2002/0179887 A1 | 12/2002 | Zeng et al. |
| 2003/0006026 A1 | 1/2003 | Matsumoto et al. |
| 2003/0024388 A1 | 2/2003 | Scharpf |
| 2003/0031291 A1 | 2/2003 | Yamamoto et al. |
| 2003/0102254 A1 | 6/2003 | Eijsbouts et al. |
| 2003/0119658 A1 | 6/2003 | Allison et al. |
| 2003/0124041 A1 | 7/2003 | Neumann et al. |
| 2003/0130360 A1 | 7/2003 | Kindig et al. |
| 2003/0153632 A1 | 8/2003 | Wang et al. |
| 2003/0180215 A1 | 9/2003 | Niu et al. |
| 2003/0188668 A1 | 10/2003 | Bland |
| 2004/0028181 A1 | 2/2004 | Charles, Jr. et al. |
| 2004/0030214 A1 | 2/2004 | Schindler et al. |
| 2004/0092784 A1 | 5/2004 | Legendre |
| 2004/0109800 A1 | 6/2004 | Pahlman et al. |
| 2004/0126293 A1 | 7/2004 | Geerlings et al. |
| 2004/0131531 A1 | 7/2004 | Geerlings et al. |
| 2004/0132833 A1 | 7/2004 | Espinoza et al. |
| 2004/0138060 A1 | 7/2004 | Rapier et al. |
| 2004/0152790 A1 | 8/2004 | Cornaro et al. |
| 2004/0154223 A1 | 8/2004 | Powell et al. |
| 2004/0197612 A1 | 10/2004 | Keefer et al. |
| 2004/0213705 A1 | 10/2004 | Blencoe et al. |

(56) References Cited

U.S. PATENT DOCUMENTS

| | | |
|---|---|---|
| 2004/0233191 A1 | 11/2004 | Mukherjee et al. |
| 2004/0244289 A1 | 12/2004 | Morozumi et al. |
| 2004/0265224 A1 | 12/2004 | Papavassiliou et al. |
| 2005/0002847 A1 | 1/2005 | Maroto-Valer et al. |
| 2005/0054880 A1 | 3/2005 | Dubois et al. |
| 2005/0175533 A1 | 8/2005 | Thomas et al. |
| 2005/0255037 A1 | 11/2005 | Otsuka et al. |
| 2005/0265912 A1 | 12/2005 | Alvarez, Jr. et al. |
| 2005/0274648 A1 | 12/2005 | Goldstein et al. |
| 2006/0021308 A1 | 2/2006 | Merkel |
| 2006/0042565 A1 | 3/2006 | Hu |
| 2006/0094593 A1 | 5/2006 | Beech et al. |
| 2007/0010588 A1 | 1/2007 | Pearson |
| 2007/0049489 A1 | 3/2007 | Becue et al. |
| 2007/0117714 A1 | 5/2007 | Geyer et al. |
| 2007/0157517 A1 | 7/2007 | Tsay et al. |
| 2007/0258878 A1 | 11/2007 | Sanfilippo et al. |
| 2008/0031809 A1 | 2/2008 | Norbeck et al. |
| 2008/0161624 A1 | 7/2008 | Glover et al. |
| 2008/0164443 A1 | 7/2008 | White et al. |
| 2008/0209807 A1 | 9/2008 | Tsangaris et al. |
| 2008/0314838 A1 | 12/2008 | Becker et al. |
| 2009/0000194 A1 | 1/2009 | Fan et al. |
| 2009/0042070 A1 | 2/2009 | Brown et al. |
| 2009/0160461 A1 | 6/2009 | Zangl et al. |
| 2010/0071262 A1 | 3/2010 | Robinson et al. |
| 2010/0119419 A1 | 5/2010 | Sprouse et al. |
| 2010/0184589 A1 | 7/2010 | Miyairi et al. |
| 2010/0187159 A1 | 7/2010 | Naunheimer |
| 2010/0258429 A1 | 10/2010 | Ugolin |
| 2010/0293845 A1 | 11/2010 | Zeman et al. |
| 2010/0332170 A1 | 12/2010 | Gao et al. |
| 2011/0005395 A1 | 1/2011 | Vimalchand et al. |
| 2011/0011720 A1 | 1/2011 | Rinker |
| 2011/0024687 A1 | 2/2011 | White et al. |
| 2011/0054049 A1 | 3/2011 | Lambert et al. |
| 2011/0094226 A1 | 4/2011 | McHugh et al. |
| 2011/0100274 A1 | 5/2011 | Kuske et al. |
| 2011/0138788 A1 | 6/2011 | Kanda et al. |
| 2011/0146152 A1 | 6/2011 | Vimalchand et al. |
| 2011/0176968 A1 | 7/2011 | Fan et al. |
| 2011/0176988 A1 | 7/2011 | Okamura et al. |
| 2011/0206469 A1 | 8/2011 | Furuyama et al. |
| 2011/0289845 A1 | 12/2011 | Davis et al. |
| 2011/0291051 A1 | 12/2011 | Hershkowitz et al. |
| 2011/0300060 A1 | 12/2011 | Guillou et al. |
| 2011/0303875 A1 | 12/2011 | Hoteit et al. |
| 2012/0167585 A1 | 7/2012 | Wormser |
| 2012/0171588 A1 | 7/2012 | Fan et al. |
| 2012/0214106 A1 | 8/2012 | Sit et al. |
| 2013/0071314 A1 | 3/2013 | Gupta |
| 2013/0085365 A1 | 4/2013 | Marashdeh et al. |
| 2013/0125462 A1 | 5/2013 | Greiner et al. |
| 2013/0149650 A1 | 6/2013 | Gauthier et al. |
| 2013/0255272 A1 | 10/2013 | Ajhar et al. |
| 2013/0261355 A1 | 10/2013 | Stamires |
| 2014/0021028 A1 | 1/2014 | Paganessi et al. |
| 2014/0134096 A1 | 5/2014 | Angelini et al. |
| 2014/0144082 A1 | 5/2014 | Fan et al. |
| 2014/0275297 A1 | 9/2014 | Velazquez-Vargas et al. |
| 2015/0238915 A1 | 8/2015 | Fan et al. |
| 2015/0291420 A1 | 10/2015 | Colozzi et al. |
| 2015/0343416 A1 | 12/2015 | Fadhel et al. |
| 2016/0002034 A1 | 1/2016 | Fan et al. |
| 2016/0016800 A1 | 1/2016 | Noyes |
| 2016/0023190 A1 | 1/2016 | Fan et al. |
| 2016/0030904 A1 | 2/2016 | Fan et al. |
| 2016/0115026 A1 | 4/2016 | Angelini et al. |
| 2016/0268616 A1 | 9/2016 | Fan et al. |
| 2017/0015554 A1 | 1/2017 | Siengchum et al. |
| 2017/0106355 A1 | 4/2017 | Colozzi et al. |
| 2018/0296978 A1 | 10/2018 | Peck et al. |
| 2018/0353933 A1 | 12/2018 | Wendland et al. |
| 2019/0003704 A1 | 1/2019 | Aranda et al. |
| 2019/0152778 A1 | 5/2019 | Fan et al. |
| 2019/0232220 A1 | 8/2019 | Fan et al. |
| 2020/0156032 A1 | 5/2020 | Fan et al. |

FOREIGN PATENT DOCUMENTS

| | | |
|---|---|---|
| CN | 1454711 A | 11/2003 |
| CN | 1501534 A | 6/2004 |
| CN | 101389734 A | 3/2009 |
| CN | 101426885 A | 5/2009 |
| CN | 102187153 A | 9/2011 |
| CN | 102388005 A | 3/2012 |
| CN | 102612625 A | 7/2012 |
| CN | 102639213 A | 8/2012 |
| CN | 102686301 A | 9/2012 |
| CN | 103468322 A | 12/2013 |
| DE | 102010028816 A1 | 11/2011 |
| EP | 0161970 A1 | 11/1985 |
| EP | 1134187 A2 | 9/2001 |
| EP | 1445018 A1 | 8/2004 |
| EP | 1580162 A2 | 9/2005 |
| EP | 1845579 A2 | 10/2007 |
| EP | 1933087 A2 | 6/2008 |
| EP | 2279785 A2 | 2/2011 |
| EP | 2441816 A1 | 4/2012 |
| EP | 2450420 A1 | 5/2012 |
| EP | 2495030 A2 | 9/2012 |
| EP | 2515038 A1 | 10/2012 |
| EP | 2601443 | 6/2013 |
| EP | 1976633 B1 | 3/2014 |
| FR | 2924035 A1 | 5/2009 |
| JP | H03-68898 A | 3/1991 |
| JP | H10249153 A | 9/1998 |
| JP | 2006-502957 A | 1/2006 |
| KR | 20060096609 A | 9/2006 |
| KR | 101364823 61 | 2/2014 |
| TW | 406055 B | 9/2000 |
| TW | 426728 B | 3/2001 |
| WO | WO1990/013773 A1 | 11/1990 |
| WO | WO1999/065097 A1 | 12/1999 |
| WO | WO2000/022690 A1 | 4/2000 |
| WO | WO2000/068339 A1 | 11/2000 |
| WO | WO2001/042132 A1 | 6/2001 |
| WO | WO2003/070629 A1 | 8/2003 |
| WO | WO2007/082089 A2 | 7/2007 |
| WO | WO2007/122498 A2 | 11/2007 |
| WO | WO2007/134075 A2 | 11/2007 |
| WO | WO2008/019079 A2 | 2/2008 |
| WO | WO2008/071215 A1 | 6/2008 |
| WO | WO2008/082312 A1 | 7/2008 |
| WO | WO2008/115076 A2 | 9/2008 |
| WO | WO2009/007200 A2 | 1/2009 |
| WO | WO2009/008565 A1 | 1/2009 |
| WO | WO2009/009388 A2 | 1/2009 |
| WO | WO2009/021258 A1 | 2/2009 |
| WO | WO2009/023515 A2 | 2/2009 |
| WO | WO2009/114309 A2 | 9/2009 |
| WO | WO2010/037011 A2 | 4/2010 |
| WO | WO2010/063923 A2 | 6/2010 |
| WO | WO2010/126617 A1 | 11/2010 |
| WO | WO2011/021161 A2 | 2/2011 |
| WO | WO2011/031752 A2 | 3/2011 |
| WO | WO2011/031755 A1 | 3/2011 |
| WO | WO2011/084734 A2 | 7/2011 |
| WO | WO2012/064712 A1 | 5/2012 |
| WO | WO2012/077978 A2 | 6/2012 |
| WO | WO2012/144899 A1 | 10/2012 |
| WO | WO2012/155054 A1 | 11/2012 |
| WO | WO2012/155059 A1 | 11/2012 |
| WO | WO2013/040645 A1 | 3/2013 |
| WO | WO2014/085243 A1 | 6/2014 |
| WO | WO2014/091024 A1 | 6/2014 |
| WO | WO2014/152814 A1 | 9/2014 |
| WO | WO2011/153568 A1 | 12/2014 |
| WO | WO2014/195904 A1 | 12/2014 |
| WO | WO2016/053941 A1 | 4/2016 |
| WO | 2017/162427 A1 | 9/2017 |

(56) References Cited

FOREIGN PATENT DOCUMENTS

| WO | 2018/166812 A1 | 9/2018 |
|---|---|---|
| WO | WO2020/210865 A1 | 10/2020 |

OTHER PUBLICATIONS

Carrero et al., "A critical literature review of the kinetics for the oxidative dehydrogenation of propane over well-defined supported vanadium oxide catalysts," ACS Catalysis, 2014, 4: 3357-3380.

Cavani et al., "Oxidative dehydrogenation of ethane and propane: How far from commercial implementation?" Catalysis Today, 2007, 127(1): 113-131.

Koulialias et al., "Ordered defects in Fe 1—x S generate additional magnetic anisotropy symmetries," Journal of Applied Physics, 2018, 123(3): 033902, 10 pages.

Moreira, "Steam Cracking: Kinetics and Feed Characterization," Dissertation, 2015, 10 pages.

Sattler et al., "Catalytic Dehydrogenation of Light Alkanes on Metals and Metal Oxides," Chem Rev, 2014, 114(20): 10613-10653.

Wang et al., "Highly efficient metal sulfide catalysts for selective dehydrogenation of isobutane to isobutene," ACS Catalysis, 2014, 4: 1139-1143.

Wang et al., "Isobutane Dehydrogenation over Metal (Fe, Co, and Ni) Oxide and Sulfide Catalysts: Reactivity and Reaction Mechanism," ChemCatChem, Jul. 2014, vol. 6, pp. 2305-2314.

Abad et al., "Chemical-looping combustion in a 300 W continuously operating reactor system using a manganese-based oxygen carrier," Fuel, 2006, vol. 85, Issue 9, pp. 1174-1185.

Abad et al., "Reduction Kinetics of CU-, Ni-, and Fe- Based Oxygen Carriers Using Syngas (CO + H2) for Chemical-Looping Combustion," Energy Fuels, 2007, 21 (4), pp. 1843-1853.

Abad et al., "The use of iron oxide as oxygen carrier in a chemical-looping reactor," Fuel, 2007, vol. 86, Issues 7-8, pp. 1021-1035.

Abdallah et al., "Comparison of mesoporous silicate supports for the immobilisation and activity of cytochrome c and lipase," J. Mol. Catal. B: Enzym., 2014, 108, 82-88.

Adanez et al., "Progress in Chemical-Looping Combustion and Reforming technologies," Progress in Energy and Combustion Science, 2012, vol. 38, Issue 2, pp. 215-282.

Adanez et al., "Selection of oxygen carriers for chemical-looping combustion," Energy & Fuels, American Chemical Society, 2004, vol. 18, No. 2, pp. 371-377.

Ahern et al., "Comparison of fenofibratemesoporous silica drug-loading processes for enhanced drug delivery," Eur. J. Pharm. Sci., 2013, 50, 400-409.

Alalwan et al., "Co3O4 nanoparticles as oxygen carriers for chemical looping combustion: A materials characterization approach to understanding oxygen carrier performance," Chemical Engineering Journal, 2017, 319, 279-287.

Alalwan et al., "α—Fe2O3 Nanoparticles as Oxygen Carriers for Chemical Looping Combustion: An Integrated Materials Characterization Approach to Understanding Oxygen Carrier Performance, Reduction Mechanism, and Particle Size Effects," Energy Fuels, 2018, 32, 7959-7970.

Anisimov et al., "Density-functional calculation of effective Coulomb interactions in metals," Phys. Rev. B, 1991, 43, 7570.

Azis et al., "On the evaluation of synthetic and natural ilmenite using syngas as fuel in chemical-looping combustion (CLC)," Chemical Engineering Research and Design, 2010, vol. 88, Issue 11, pp. 1505-1514.

Balasubramanian et al., "Hydrogen from methane in a single-step process," Chem Engr Science, 1999, 54(15-16), 3543.

Barreca et al., "Methanolysis of styrene oxide catalysed by a highly efficient zirconium-doped mesoporous silica," Appl. Catal. A, 2006, 304, 14-20.

Bell et al., "H2 Production via Ammonia Decomposition Using Non-Noble Metal Catalysts: A Review," Top Catal, 2016, 59, 1438-1457.

Burke et al., "Large pore bi-functionalised mesoporous silica for metal ion pollution treatment," J. Hazard. Mater., 2009, 164, 229-234.

Cao et al., "Investigation of Chemical Looping Combustion by Solid Fuels. 1. Process Analysis," Energy Fuels, 2006, 20(5), pp. 1836-1844.

Cheng et al., "Carbon Dioxide Adsorption and Activation on Ceria (110): A density functional theory study," J. Chem. Phys. 2013, 138, 014702.

Cheng et al., "Methane Adsorption and Dissociation on Iron Oxide Oxygen Carrier: Role of Oxygen Vacancy," Phys. Chem. Chem. Phys. 2016, 18, 16423-16435.

Cheng et al., "Oxygen vacancy promoted methane partial oxidation over iron oxide oxygen carrier in chemical looping process," Phys. Chem. Chem. Phys., 2016, 18, 32418-32428.

Cheng et al., "Propagation of Olefin Metathesis to Propene on WO3 Catalysts: A Mechanistic and Kinetic Study," ACS Catal. 2015, 5, 59-72.

Cho et al., "Comparison of iron-, nickel-, copper- and manganese-based oxygen carriers for chemical-looping combustion," Fuel, 2004, vol. 83, Issue 9, pp. 1215-1225.

Chung et al., "Chemically and physically robust, commercially-viable iron-based composite oxygen carriers sustainable over 3000 redox cycles at high temperatures for chemical looping applications," Energy Environ. Sci., 2017, 10, 2318-2323.

Coleman et al., "Synthesis and characterization of dimensionally ordered semiconductor nanowires within mesoporous silica," J. Am. Chem. Soc., 2001, 123, 7010-7016.

Connell et al., "Process Simulation of Iron-Based Chemical Looping Schemes with CO2 Capture for Hydrogen and Electricity Production from Coal," Presented at 29th Annual International Pittsburgh Coal Conference, Pittsburgh, PA, Oct. 15-18 (2012), pp. 1274-1281.

De Diego et al., "Development of Cu-based oxygen carriers for chemical-looping combustion," Fuel, 2004, vol. 83, Issue 13, pp. 1749-1757.

De Klerk, "Gas-to-Liquid Conversion." Natural Gas Conversion Technologies Workshop of ARPA-E. U.S. Department of Energy, Houston, TX. vol 13 (2012).

Delaney et al., "Development of chemically engineered porous metal oxides for phosphate removal," J. Hazard. Mater., 2011, 185, 382-391.

Delaney et al., "Porous silica spheres as indoor air pollutant scavengers," J. Environ. Monit., 2010, 12, 2244-2251.

Denton et al., "Simultaneous Production of High-Purity Hydrogen and Sequestration-Ready CO2 from Syngas," 2003.

EIA—Independent Statistics and Analysis. U.S. Department of Energy, U.S. Energy Information Administration "Annual Energy Outlook 2015 with Projections to 2040," Apr. 2015.

EIA—Independent Statistics and Analysis. U.S. Department of Energy, U.S. Energy Information Administration, "How Much Petroleum Does the United States Import and from Where?" <https://www.eia.gov/tools/faqs/faq.php?id=727&t=6> webpage available as early as Mar. 22, 2017.

EIA—Independent Statistics and Analysis. U.S. Department of Energy, U.S. Energy Information Administration, "Natural Gas Vented and Flared." <https://www.eia.gov/dnav/ng/NG_PROD_SUM_A_EPG0_VGV_MMCF_A.htm> webpage available as early as Feb. 29, 2016.

EIA—Independent Statistics and Analysis. U.S. Department of Energy, U.S. Energy Information Administration, "Natural Gas Weekly Update." <https://www.eia.gov/naturalgas/weekly/> webpage available as early as Dec. 4, 2011.

Environmental Protection Agency, "Geological CO2 Sequestration Technology and Cost Analysis," Technical Support Document, pp. i-vi & pp. 1-61, Jun. 2008.

Faezad Othman et al., "Utilization of Low-Grade Iron Ore in Ammonia Decomposition," Procedia Chemistry, 2016, 19:119-124.

Faezad Othman et al., "Utilization of Malaysian Low Grade Iron Ore as Medium for Ammonia Decomposition," ARPN Journal of Engineering and Applied Sciences, 2015, 10(22):17286-17288.

(56) References Cited

OTHER PUBLICATIONS

Fan et al., "Chemical looping processes for CO2 capture and carbonaceous fuel conversion prospect and opportunity," Energy Environmental Science, 2012, p. 7254-7280.

Fan et al., "Utilization of chemical looping strategy in coal gasification processes," Particuology, 2008, vol. 6, Issue 3, pp. 131-142.

Fan et al., "Chemical-Looping Technology Platform," AIChE Journal, 61(1), 2-22 (2015).

Fan, "Chemical Looping Systems for Fossil Energy Conversions," Wiley-AIChE: Hoboken, NJ, U.S.A.; 2010.

Flynn et al., "Pervaporation performance enhancement through the incorporation of mesoporous silica spheres into PVA membranes," Sep. Purif. Technol., 2013, 118, 73-80.

Forero et al., "Syngas combustion in a 500 Wth Chemical-Looping Combustion system using an impregnated Cu-based oxygen carrier," Fuel Processing Technology, 2009, vol. 90, Issue 12, pp. 1471-1479.

Forzatti, "Present status and perspectives in de-NOx SCR catalysis." Appl. Catal. A: Gen., 222(1-2), 2001, 221-236.

Gao et al., "Production of syngas via autothermal reforming of methane in a fluidized-bed reactor over the combined $CeO_2$-$ZrO_2$/$SiO_2$ supported Ni catalysts," International Journal of Hydrogen Energy, 2008, vol. 33, p. 5493-5500.

Garcia-Labiano et al., "Temperature variations in the oxygen carrier particles during their reduction and oxidation in a chemical-looping combustion system," Chemical Engineering Science, 2005, vol. 60, No. 3, pp. 851-862.

Geldart, "Types of Gas Fluidization," Power Technology, vol. 7, pp. 285-292, 1973.

Ghanapragasam et al., "Hydrogen production from coal direct chemical looping and syngas chemical looping combustion systems: Assessment of system operation and resource requirements," International Journal of Hydrogen Energy, 2009, vol. 34, Issue 6, pp. 2606-2615.

Ghoneim et al., "Review on innovative catalytic reforming of natural gas to syngas," World J. Eng. Technol, 2016, 4(1):116-139.

Go et al., "Hydrogen production from two-step steam methane reforming in a fluidized bed reactor," International Journal of Hydrogen Energy, 2009, vol. 34, p. 1301-1309.

Goellner et al., "Baseline analysis of crude methanol production from coal and natural gas," National Energy Technology Laboratory (NETL), US Department of Energy, 2014, 83 pages.

Goellner, J. F., V. Shah, M. J. Turner, N. J. Kuehn, J. Littlefield, G. Cooney, and J. Marriott, "Analysis of Natural Gas-to Liquid Transportation Fuels via Fischer-Tropsch," United States Department of Energy/NETL, DOE/NETL-2013/1597, Pittsburgh, PA (2013).

Grimme et al., "A consistent and accurate ab initio parametrization of density functional dispersion correction (DFT-D) for the 94 elements H-Pu," J. Chem. Phys., 2010, 132, 19.

Grimme et al., "Effect of the damping function in dispersion corrected density functional theory," J. Comput. Chem., 2011, 32, 1456-1465.

Haque, "Microwave energy for mineral treatment processes—a brief review," International Journal of Mineral Processing, vol. 57, pp. 1-24, 1999.

Henkelman et al., "A climbing image nudged elastic band method for finding saddle points and minimum energy paths," J. Chem. Phys., 2000, 113, 9901-9904.

Herbst et al., "Relativistic calculations of 4f excitation energies in the rare-earth metals: Further results," Phys. Rev. B, 1978, 17, 3089.

Herzog, "Carbon Sequestration via Mineral Carbonation: Overview and Assessment," MIT Laboratory for Energy and the Environmental, http://sequestration.mit.edu/pfd/carbonates.pdf, Mar. 14, 2002.

Hildebrandt et al., "Producing Transportation Fuels with Less Work," Science, Mar. 27, 2009, vol. 323, pp. 1680-1681.

Hossain et al., "Chemical-looping combustion (CLC) for inherent CO2 separations—a review," Chemical Engineering Science, 2008, vol. 63, Issue 18, pp. 4433-4451.

Hua et al., "Three Dimensional Analysis of Electrical Capacitance Tomography Sensing Fields," 1999 IOP Publishing LTD, vol. 10, pp. 717-725.

Huijgen et al., "Carbon dioxide sequestration by mineral carbonation," ECN-C--03-016, www.ecn.nl/docs/library/report/200e/c03016.pdf, Feb. 2003.

Hung et al., "Zeolite ZSM-5 Supported Bimetallic Fe-Based Catalysts for Selective Catalytic Reduction of NO: Effects of Acidity and Metal Loading," Advanced Porous Materials, 2016, 4(3): 189-199(11).

Imanaka et al., "Advances in Direct NOx Decomposition Catalysts," Appl. Catal. A: Gen., 431-432, 2012, 1-8.

Ishida et al., "Evaluation of a Chemical-Looping-Combustion Power-Generation System by Graphic Exergy Analysis," Energy, 12(2), 147-154 (1987).

Iwamoto et al., "Influence of sulfur dioxide on catalytic removal of nitric oxide over copper ion-exchanged ZSM-5 Zeolite." Appl. Catal., 69(2), 1991, 15-19.

Izquierdo et al., "Catalyst Deactivation and Regeneration Processes in Biogas Tri-Reforming Process. The Effect of Hydrogen Sulfide Addition," Catalysts, 2018, 8(12): 19 pages.

Jadhav et al., "Carbonation of Mg-Bearing Minerals: Kinetic and Mechanistic Studies," Ohio Coal Research Consortium/Ohio State University Project C3.12, www.ohiocoal.org/projects/year3/c3.12, Jul. 3, 2002.

Jin et al., "Development of a Novel Chemical-Looping Combustion: Synthesis of a Looping Material with a Double Metal Oxide of CoO—NiO," Energy & Fuels, 1998, vol. 12, 1272-1277.

Johansson et al., "Combustion of Syngas and Natural Gas in a 300 W Chemical-Looping Combustor," Chemical Engineering Research and Design vol. 2006, vol. 84, Issue 9, pp. 819-827.

Kaiser et al., "Precombustion and Postcombustion Decarbonization," IEEE, Power Engineering Review, Apr. 2001, pp. 15-17.

Kathe et al., "Modularization strategy for syngas generation in chemical," AIChE Journal, 2017, 63(8):3343-3360.

Kathe et al., "Chemical Looping Gasification for Hydrogen Enhanced Syngas Production with in-situ CO2 Capture," United States Department of Energy, OSTI: 1185194, (2015).

Kiuchi et al., "Recovery of hydrogen from hydrogen sulfide with metals or metal sulfides," Int. J. Hydrogen Energy, 1982, 7: 477-482.

Kresse et al., "Ab initio molecular dynamics for liquid metals," Phys. Rev. B, 1993, 47, 558.

Kresse et al., "Efficiency of ab-initio total energy calculations for metals and semiconductors using a plane-wave basis set," Comput. Mater. Sci., 1996, 6, 15-50.

Kresse et al., "Efficient iterative schemes for ab initio total-energy calculations using a planewave basis set," Phys. Rev. B, 1996, 54, 11169.

Kumar et al., "Direct air capture of CO2 by physisorbent materials," Angew. Chem., Int. Ed., 2015, 54, 14372-14377.

Leion et al., "Solid fuels in chemical-looping combustion using oxide scale and unprocessed iron ore as oxygen carriers," Fuel, 2009, vol. 88, Issue 10, pp. 1945-1954.

Leion et al., "Solid fuels in chemical-looping combustion," International Journal of Greenhouse Gas Control, 2008, vol. 2, Issue 2, pp. 180-193.

Leion et al., "The use of petroleum coke as fuel in chemical-looping combustion," Fuel, 2007, vol. 86, Issue 12-13, pp. 1947-1958.

Li et al., "Clean coal conversion processes—progress and challenges," The Royal Society of Chemistry, Energy & Environmental Science, Jul. 30, 2008, vol. 1, pp. 248-267.

Li et al., "Ionic Diffusion in the Oxidation of Iron-effect of Support and Its Implications to Chemical Looping Applications," Energy Environ. Sci. 2011, 4, 876-880.

Li et al., "Role of Metal Oxide Support in Redox Reactions of Iron Oxide for Chemical Looping Applications: Experiments and Density Functional Theory Calculations," Energy Environmental Science, 2011, vol. 4, p. 3661-3667.

Li et al., "Syngas chemical looping gasification process: Bench-scale studies and reactor simulations," AICHE Journal, 2010, vol. 56, Issue 8, pp. 2186-2199.

(56) References Cited

OTHER PUBLICATIONS

Li et al., "Syngas Chemical Looping Gasification Process: Oxygen Carrier Particle Selection and Performance," Energy Fuels, 2009, 23(8), pp. 4182-4189.

Lin et al., "Novel Magnetically Separable Mesoporous Fe2O3@SBA-15 Nanocomposite with Fully Open Mesochannels for Protein Immobilization," Chemistry of Materials, 2008, vol. 20, pp. 6617-6622.

Liu et al., "Enhanced Performance of Alkali Metal Doped Fe2O3 and Fe2O3/Al2O3 Composites as Oxygen Carrier Material in Chemical Looping Combustion," Energy Fuels. 2013, 27, 4977-4983.

Liu et al., "Recent Advances in Catalytic DeNOx Science and Technology," Catalysis Reviews, 48(1), 2006, 43-89.

Lockwood Greene, "Ironmaking Process Alternative Screening Study, vol. I: Summary Report," Department of Energy United States of America, Oct. 2000, 153 pages.

Luo et al., "Shale Gas-to-Syngas Chemical Looping Process for Stable Shale Gas Conversion to High Purity Syngas with H2:CO Ratio of 2:1," Energy and Environmental Science, 7(12), 4104-4117, (2014).

Lyngfelt, "Chemical Looping Combustion of Solid Fuels—Status of Development," Applied Energy, 2014, vol. 113, p. 1869-1873.

Lyngfelt, "Oxygen Carriers for Chemical Looping Combustion Operational Experience," 1st International Conference on Chemical Looping, Mar. 2010.

Makepeace et. al., "Ammonia decomposition catalysis using non-stoichiometric lithium imide," Chem. Sci., 2015, 6, 3805.

Mamman et al., "Simultaneous steam and CO2 reforming of methane to syngas over NiO/MgO/SA-5205 in presence and absence of oxygen," Applied Catalysis A, 1998, vol. 168, p. 33-46.

Mao et al., "Facile synthesis of phase-pure FeCr$_2$Se$_4$ and FeCr$_2$S$_4$ nanocrystals via a wet chemistry method," J. Mater. Chem. C, 2014, 2: 3744-3749.

Marashdeh, Q. et al., "A Multimodal Tomography System Based on ECT Sensors," IEEE Sensors Journal, vol. 7, No. 3, 2007, 426-433.

Marashdeh, Q., Advances in Electrical Capacitance Tomography, Dissertation, The Ohio State University, 2006.

Masui et al.,"Direct Decomposition of NO into N2 and O2 Over C-type Cubic Y2O3-Tb4O7-ZrO2," Materials Sciences and Applications, 3(10), 2012, 733-738.

Mattisson et al., "Application of chemical-looping combustion with capture of CO2," Second Nordic Minisymposium on Carbon Dioxide Capture and Storage, Goeteborg, Oct. 26, 2001, pp. 46-51.

Mattisson et al., "Chemical-looping combustion using syngas as fuel," International Journal of Greenhouse Gas control, 2007, vol. 1, Issue 2, pp. 158-169.

Mattisson et al., "CO 2 capture from coal combustion using chemical-looping combustion—Reactivity investigation of Fe, Ni and Mn based oxygen carriers using syngas," Department of Energy and Environment, Division of Energy Technology and Department of Chemical and Biological Engineering, Division of Environmental Inorganic Chemistry, Chalmers University of Technology, 2007.

Mattisson et al., "Reactivity of Some Metal Oxides Supported on Alumina with Alternating Methane and Oxygen—Application for Chemical-Looping Combustion," Energy & Fuels, 2003, vol. 17, pp. 643-651.

Mattisson et al., "The use of iron oxide as an oxygen carrier in chemical-looping combustion of methane with inherent separation of CO2," Fuel, 2001, vol. 80, pp. 1953-1962.

Mattisson et al., "Use of Ores and Industrial Products as Oxygen Carriers in Chemical-Looping Combustion," Energy & Fuels, 2009, vol. 23, pp. 2307-2315.

Mihai et al., "Chemical looping methane partial oxidation: The effect of the crystal size and O content of LaFeO3," Journal of Catalysis, 2012, 293:175-185.

Miller et al., "Toward Transformational Carbon Capture," AIChE Journal, 62, 1-10 (2016).

NETL, National Energy Technology Laboratory. U.S. Department of Energy, "Quality Guidelines for Energy System Studies—Specification for Selected Feedstocks." Jan. 2012.

NETL, National Energy Technology Laboratory. U.S. Department of Energy, "Syngas Contaminant Removal and Conditioning," webpage accessed on Jul. 8, 2018.

Nipattummakul et al., "Hydrogen and syngas production from sewage sludge via steam gasification," Fuel and Energy Abstracts, 2010, 35 (21), 11738-11745.

Ockwig et al., "Membranes for Hydrogen Separation," American Chemical Society, Chem. Rev., Oct. 10, 2007, vol. 107, pp. 4078-4110.

O'Connor et al., "Carbon Dioxide Sequestration by Direct Mineral Carbonation: Results from Recent Studies and Currents Status," Abstract, USDOE Office of Fossil Energy, 2001.

Ohio Coal Development Office of the Ohio Air Quality Development Authority, "Ohio Coal Research Consortium (OCRC)—IV, Year 3 Proposal Solicitation," http://www.ohioquality.org/ocdo/other_pdf/Consortium_IV_Year_3_RFP.pdf (2006).

Ortiz et al., "Hydrogen Production by Auto-Thermal Chemical-Looping Reforming in a Pressurized Fluidized Bed Reactor Using Ni-based Oxygen Carriers," International Journal of Hydrogen Energy, 2010, vol. 35, p. 151-160.

Osha, "Hydrogen Sulfide in Workplaces," <https://www.osha.gov/SLTC/hydrogensulfide/hydrogensulfide_found.html> webpage accessed Jul. 8, 2018.

Pans et al., "Optimization of H2 production with CO2 capture by steam reforming of methane integrated with a chemical-looping combustion system," International Journal of Hydrogen Energy, 2013, 38(27): 11878-11892.

Park et al., "CO2 Mineral Sequestration: Chemically Enhanced Aqueous Carbonation of Serpentine," The Canadian Journal of Chemical Engineering, 2003, vol. 81, pp. 885-890.

Park et al., "CO2 Mineral Sequestration: physically activated dissolution of serpentine and pH swing process," Chemical Engineering Science, 2004, vol. 59, pp. 5241-5247.

Perdew et al., "Generalized gradient approximation made simple," Phys. Rev. Lett., 1996, 77, 3865.

Pfeifer, "Industrial furnaces-status and research challenges," Energy Procedia, 2017, 120: 28-40.

Pröll et al., "Syngas and a separate nitrogen/argon stream via chemical looping reforming—A 140 kW pilot plant study," Fuel, 2010, vol. 89, Issue 6, pp. 1249-1256.

Qin et al., "Enhanced methane monversion in mhemical looping partial oxidation systems using a copper doping modification," Appl. Catal. B, 2018, 235, 143-149.

Qin et al., "Evolution of Nanoscale Morphology in Single and Binary Metal Oxide Microparticles During Reduction and Oxidation Processes," J. Mater. Chem. A. 2014, 2, 17511-17520.

Qin et al., "Impact of 1% Lathanum Dopant on Carbonaceous Fuel Redox Reactions with an Iron-Based Oxygen Carrier in Chemical Looping Processes," ACS Energy Letters, 2017, 2, 70-74.

Qin et al., "Nanostructure Formation Mechanism and Ion Diffusion in Iron-Titanium Composite Materials with Chemical Looping Redox Reactions," J. Mater. Chem. A. 2015, 3, 11302-11312.

Quin et al., "Improved Cyclic redox reactivity of lanthanum modified iron-based oxygen carriers in carbon monoxide xhemical looping combustion," Journal of Materials Chemistry A, 2017, 8 pages.

Rollmann et al., "First-principles calculation of the structure and magnetic phases of hematite," Phys. Rev. B, 2004, 69, 165107.

Rostrup-Nielsen, "Syngas in Perspective," Catalysis Today, 2002, 71(3-4), 243-247.

Ruchenstein et al., "Carbon dioxide reforming of methane over nickel/alkaline earth metal oxide catalysts," Applied Catalysis A, 1995, vol. 133, p. 149-161.

Russo et al., "Impact of Process Design of on the Multiplicity Behavior of a Jacketed Exothermic CSTR," AICHE Journal, Jan. 1995, vol. 41, No. 1, pp. 135-147.

Ryden et al., "Synthesis gas generation by chemical-looping reforming in a continuously operating laboratory reactor," Fuel, 2006, vol. 85, p. 1631-1641.

(56) References Cited

OTHER PUBLICATIONS

Ryden et al., "Using steam reforming to produce hydrogen with carbon dioxide capture by chemical-looping combustion," International Journal of Hydrogen Energy, 2006, 31(10): 1271-1283.
Sassi et al., "Sulfur Recovery from Acid Gas Using the Claus Process and High Temperature Air Combustion ( HiTAC ) Technology," Am. J. Environ. Sci., 2008, 4, 502-511.
Scott et al., "In situ gasification of a solid fuel and CO2 separation using chemical looping," AICHE Journal, 2006, vol. 52, Issue 9, pp. 3325-3328.
Shen et al., "Chemical-Looping Combustion of Biomass in a 10kWth Reactor with Iron Oxide as an Oxygen Carrier," Energy & Fuels, 2009, vol. 23, pp. 2498-2505.
Shen et al., "Experiments on chemical looping combustion of coal with a NiO based oxygen carrier," Combustion and Flame, 2009, vol. 156, Issue 3, pp. 721-728.
Sheppard et al., "Paths to which the nudged elastic band converges," J. Comput. Chem., 2011, 32, 1769-1771.
Shick et al., "Single crystal growth of $CoCr_2S_4$ and $FeCr_2S_4$," Journal of Crystal Growth, 1969, 5(4): 313-314.
Speight, "Gasification processes for syngas and hydrogen production," Gasification for Synthetic Fuel Production, Woodhead Publishing, 2015, 119-146.
Sridhar et al., "Syngas Chemical Looping Process: Design and Construction of a 25 kWth Subpilot Unit," Energy Fuels, 2012, 26(4), pp. 2292-2302.
Steinfeld et al., "Design Aspects of Solar Thermochemical Engineering—A case Study: Two-Step Water-Splitting Cycle Using the Fe3O4/FeO Redox System," Solar Energy, 1999, pp. 43-53.
Steinfeld, "Solar hydrogen production via a two-step water-splitting thermochemical cycle based on Zn/ZnO redox reactions," International Journal of Hydrogen Energy, 2002, vol. 27, pp. 611-619.
Sun et al., "Review: Fundamentals and challenges of electrochemical CO2 reduction using two-dimensional materials," Chem, 2017, 3, 560-587.
Takanabe, "Catalytic Conversion of Methane: Carbon Dioxide Reforming and Oxidative Coupling," Journal of the Japan Petroleum Institute, 2012, 55, 1-12.
Thiollier et al., "Preparation and Catalytic Properties of Chromium-Containing Mixed Sulfides," Journal of Catalysis, 2011, 197(1): 58-67.
Tian et al., "Thermodynamic investigation into carbon deposition and sulfur evolution in a Ca-based chemical-looping combustion system," Chemical Engineering Research & Design, 2011, vol. 89, Issue 9, p. 1524.
Trout et al., "Analysis of the Thermochemistry of NOx Decomposition over CuZSM-5 Based on Quantum Chemical and Statistical Mechanical Calculations," J. Phys. Chem, 100(44), 1996, 17582-17592.
U.S. Department of Energy, NCCTI Energy Technologies Group, Office of Fossil Energy, "CO2 Capture and Storage in Geologic Formations," pp. 34, Revised Jan. 8, 2002.
United States Environmental Protection Agency. "Air Pollution Control Technology Fact Sheet: Selective Catalytic Reforming," <https://www3.epa.gov/ttncatc1/cica/files/fscr.pdf> (2003).
Usachev et al., "Conversion of Hydrocarbons to Synthesis Gas: Problems and Prospects," Petroleum Chemistry, 2011, vol. 51, p. 96-106.
Velazquez-Vargas et al., "Atmospheric Iron-based Coal Direct Chemical Looping (CDCL) Process for Power Generation", presented in Power-Gen International 2012, Orlando, FL, Dec. 11-13, 2012, BR-1892, 1-5.
Vernon et al., "Partial Oxidation of Methane to Synthesis Gas," Catalysis Letters, 1990, vol. 6, p. 181-186.
Wang et al., "Study of bimetallic interactions and promoter effects of FeZn, FeMn and FeCr Fischer—Tropsch synthesis catalysts," Journal of Molecular Catalysis A: Chemical, 2010, 326:29-40.
Warsito, W. et al., Electrical Capacitance Volume Tomography, 2007, pp. 1-9.
Watanabe, "Electrical properties of $FeCr_2S_4$ and $CoCr_2S_4$," Solid State Communications, 1973, 12(5): 355-358.
Xu et al., "A novel chemical looping partial oxidation process for thermochemical conversion of biomass to syngas," Applied Energy, 2018, 222:119-131.
Yamazaki et al., "Development of highly stable nickel catalyst for methane-steam reaction under low steam to carbon ratio," Applied Catalyst A, 1996, vol. 136, p. 49-56.
Yin et al., "A mini-review on ammonia decomposition catalysts for on-site generation of hydrogen for fuel cell applications," Applied Catalysis A: General, 2004, 277, 1-9.
Zafar et al., "Integrated Hydrogen and Power Production with CO2 Capture Using Chemical-Looping ReformingRedox Reactivity of Particles of CuO, Mn2O3, NiO, and Fe2O3 Using SiO2 as a Support," Ind. Eng. Chem. Res., 2005, 44(10), pp. 3485-3496.
Zeng et al., "Metal oxide redox chemistry for chemical looping processe," Nat Rev Chem., 2018, 2, 349-364.
United States Patent Office Action for U.S. Appl. No. 17/251,998 dated Mar. 18, 2022 (11 pages).

ALKENE GENERATION USING METAL SULFIDE PARTICLES

CROSS-REFERENCE TO RELATED APPLICATION(S)

The present application is a U.S. national stage entry of International Patent Application No. PCT/US2020/027324, filed on Apr. 8, 2020, which claims priority to U.S. Provisional Patent Application No. 62/831,617, filed on Apr. 9, 2019, the entire contents of each of which are fully incorporated herein by reference.

TECHNICAL FIELD

The present disclosure relates to systems and methods for alkene generation. More particularly, the present disclosure relates to systems and methods for alkene generation using reducible metal sulfide particles.

INTRODUCTION

Alkanes exhibit a tendency to dehydrogenate to alkenes at high temperatures through an endothermic reaction. Industrially, this is accomplished by the steam cracking process and is commonly used for non-catalytic conversion of ethane to ethylene. Thermal cracking or steam cracking relies on thermally activating the hydrocarbon feedstock to produce cracked or smaller hydrocarbons or unsaturated hydrocarbons. The cracking process takes place by gas phase radical mechanism, where the hydrocarbon radicals undergo initiation, propagation and termination steps. Typically, longer hydrocarbon chain cracking reactions to smaller hydrocarbons are preferred over unsaturated hydrocarbons. Thus, propane or higher alkanes tend to produce ethylene instead of their respective alkenes, and therefore require a catalyst to ensure that the desired alkene product is the kinetically favored product.

Taking the example of propylene production, the most common and commercially available method is propane dehydrogenation (PDH). The basic principle involves dehydrogenation of propane over a catalyst to form propylene and hydrogen, as shown in equation 1 below.

$$C_3H_8 \xrightarrow{Catalyst, \Delta} C_3H_6 + H_2 \qquad (1)$$

This reaction is performed at a lower temperature than in steam cracking reactions, catalyzing the C—H bond activation in propane with no or minimal C—C bond activation. These PDH processes typically are run in either fixed bed reactors or fluidized bed reactors at temperatures ranging from 500-700° C. and pressures from 0.5-3 bar. Out of the several commercially available systems, two processes have been highlighted in this section. The Catofin process, by Lummus, which uses a $CrO_x$ on $Al_2O_3$ catalyst with Na/K as promoters and the Oleflex process, by UOP, which uses a Pt—Sn alloy on $Al_2O_3$ catalyst with Na/K promoters. Both of these processes suffer from carbon deposition on the catalyst, and subsequent gradual catalyst deactivation.

Reactivation of a deactivated catalyst either requires reducing the catalyst with hydrogen, or using chlorine gas to disperse the sintered active sites, where the carbon is typically burnt off with air oxidation. Additionally, as seen from FIG. 1, the PDH process for all alkanes is limited by the thermodynamic equilibrium of the reaction in equation 1. Thus, in order to achieve higher propane conversions, the reaction would need to be run at a higher temperature. However, higher temperatures tend to favor C—C bond activation, reducing the selectivity and limiting the operational matrix of the process.

In order to address this trade-off, several catalytic technologies have been developed which introduce an oxidizing gas into the system, thus creating a sink for hydrogen. This allows for higher conversion of the alkane in order to restore the dehydrogenation equilibrium. This process is known as oxidative dehydrogenation (ODH) and is widely used for ethane and propane dehydrogenation in the presence of molecular oxygen. This molecular oxygen assisted ODH process relies on utilizing oxygen to extract H from an alkane, such as propane, to convert it to propylene and have water and heat as by-products. Due to the electronegativity difference, this reaction, shown in equation (2), theoretically occurs at a lower temperature than PDH technology.

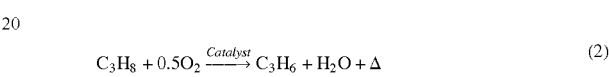
$$C_3H_8 + 0.5O_2 \xrightarrow{Catalyst} C_3H_6 + H_2O + \Delta \qquad (2)$$

However, using a strong oxidant, such as $O_2$, negatively affects the selectivity due to the formation of undesired products, such as CO and $CO_2$. As a result, a majority of the $O_2$—ODH catalysts fail to meet the performance of PDH catalysts, where selectivity drops sharply with an increase in propane conversion. As an alternative, sulfur or sulfur derivatives, such as $H_2S$, are used which resemble a softer oxidant. Transition state metal sulfide catalysts have been shown to be active towards conversion of butane to isobutene. These sulfide catalysts have a lower activation energy barrier for C—H activation than C—C bond activation, making them much more effective than the PDH catalysts. However, as these catalysts react with the alkane, some sulfur is lost as $H_2S$, thus reducing the catalyst activity. Some sulfide catalysts have been reported for propane to propylene conversion which operate by co-feeding $H_2S$ and $H_2$ with propane. However, these catalysts also require a regeneration step with air followed by $H_2S$ and $H_2$ mixture to regain the active metal sulfide catalyst.

A major drawback of the catalytic ODH system is that the oxidant stream and the alkane stream must be co-fed in the reactor. This results in the formation of undesired side products, which decrease the selectivity of the desired alkene. Also, in the case of sulfur, the metal sulfide catalyst may lose its activity as the catalyst reduction reactions dominate the catalyst oxidation reactions. This imbalance results in the use of extreme catalyst regeneration steps, limiting the efficiency and turnover of the process.

SUMMARY

Generally, the instant disclosure relates to alkene generation using metal sulfide particles. In one aspect, a method can include providing a gaseous alkane input stream to a first reactor and providing a metal sulfide ($MS_x$) particle to the first reactor, whereupon the metal sulfide ($MS_x$) particle reacts with an alkane in the gaseous alkane input stream to generate an alkene, a reduced metal sulfide ($MS_{x-1}$) particle, and at least one of: hydrogen sulfide ($H_2S$) and a sulfur containing compound. The method can also include collecting a product stream from the first reactor including the alkene, hydrogen sulfide ($H_2S$) and/or the sulfur containing compound, providing the reduced metal sulfide ($MS_{x-1}$) particle to a second reactor, providing a sulfur stream to the second reactor, whereupon the reduced metal sulfide ($MS_{x-1}$) particle reacts with sulfur in the sulfur stream to generate the metal sulfide ($MS_x$) particle and hydrogen ($H_2$). Then a second reactor output stream including hydrogen ($H_2$) can be collected.

In another aspect, a method can include providing a gaseous alkane input stream to a reactor, the reactor including a metal sulfide ($MS_x$) particle, whereupon the metal sulfide ($MS_x$) particle reacts with an alkane in the gaseous alkane input stream to generate an alkene, a reduced metal sulfide ($MS_{x-1}$) particle, and at least one of: hydrogen sulfide ($H_2S$) and one or more sulfur containing compounds selected from: $S_2$, CS, and $CS_2$. The method can also include collecting a product stream from the reactor including the alkene, hydrogen sulfide ($H_2S$) and/or the one or more sulfur containing compounds, after collecting the product stream, providing an inert gas stream to the reactor, after providing the inert gas stream to the reactor, providing a sulfur stream to the reactor, whereupon the reduced metal sulfide ($MS_{x-1}$) particle reacts with sulfur in the sulfur stream to generate the metal sulfide ($MS_x$) particle and hydrogen ($H_2$), and collecting a reactor output stream including hydrogen ($H_2$).

There is no specific requirement that a material, technique or method relating to alkene generation include all of the details characterized herein, in order to obtain some benefit according to the present disclosure. Thus, the specific examples characterized herein are meant to be exemplary applications of the techniques described, and alternatives are possible.

DETAILED DESCRIPTION

Figure 1:
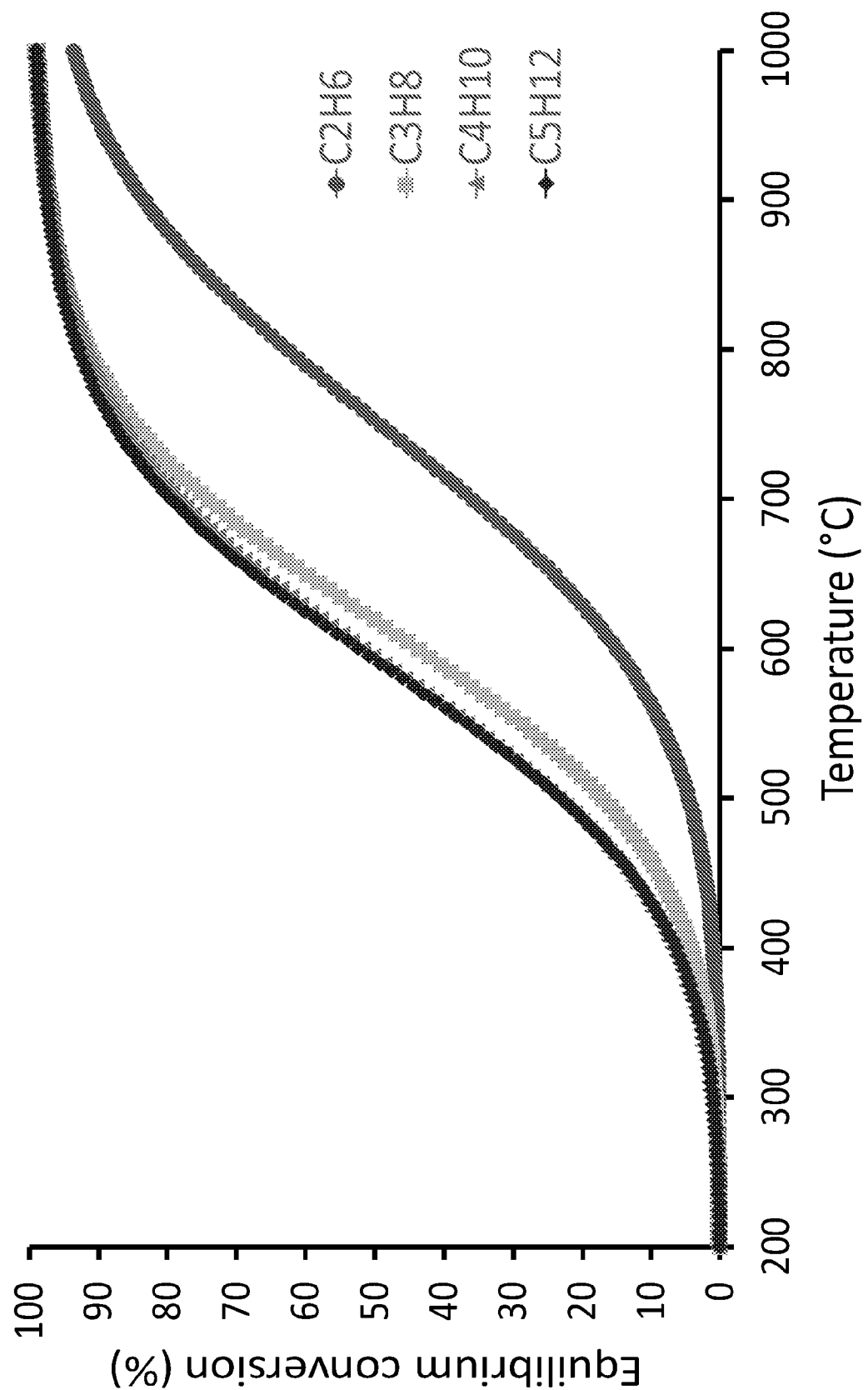
FIG. 1 is a graph showing thermodynamic equilibrium for alkane conversion to alkene via dehydrogenation.

Systems and methods disclosed and contemplated herein relate to alkene generation. Disclosed systems and methods employ reducible metal sulfides during conversion of alkanes to alkenes, typically in a chemical looping reactor system. Some implementations can utilize two reactor systems. Some implementations can utilize single, fixed bed reactor systems.

In certain aspects, systems and methods disclosed herein address one or more drawbacks of catalytic ODH reactions by splitting an oxidant stream and an alkane stream. In some instances, those streams are provided to two reactors operating independent of each other. In some instances, those streams are sequentially provided to a single reactor. Generally, an alkane or a mixture of alkanes reacts with a metal sulfide ($MS_x$) to form the alkene, $H_2S$ and/or a sulfur containing compound in a reactor. Here M is the metal component of the metal sulfide and S represents the sulfur in the solid lattice. Thus, the metal sulfide acts as the sulfur source that carries out the oxidation of $H_2$ to $H_2S$, thus improving the alkane conversion.

During exemplary operation of a two reactor system, the $MS_x$ can reduce to $MS_{x-1}$, which is sent to the sulfidation reactor where a sulfur source regenerates the metal sulfide into its original form, i.e. $MS_2$. This regeneration is different from the regeneration steps in a catalytic system, because this operation is a part of the chemical looping structure. The regeneration step in a catalytic system is carried out to address the loss of reactivity of the catalyst under non-ideal and unstable conditions. However, an ideal catalyst would portray a stable performance, without requiring a regeneration step. The chemical looping mode, however, intentionally carries out the reduction and oxidation reactions and the oxidation or regeneration reaction is performed to complete the loop. In other words, the metal sulfide can be considered as a sulfur carrier between the two reactors, where the two reactors follow very different reaction mechanisms. The regeneration reactor is also capable of producing a value-added product such as $H_2$, which is not the case in the catalytic system. The chemical looping mode thus allows for the two reactors to be governed by different thermodynamic and kinetic factors based on their operating parameters.

I. CHEMICAL ASPECTS

Systems and methods of the present disclosure may include input streams provided to reactor systems and output streams generated by reactor systems. The sections below discuss various chemical aspects of exemplary systems and methods.

A. Input Streams

Exemplary reactor systems may receive a gaseous alkane input stream and a sulfur stream. In two reactor configurations, exemplary reactors may also receive metal sulfide particles.

Gaseous alkane input streams may include one alkane species or may be a mixture of alkane species. As implied, alkanes in gaseous alkane input streams are in a gaseous phase.

Alkanes usable in gaseous alkane input streams may be linear, branched, or cyclic. In some implementations, gaseous alkane input streams may include at least one $C_2$-$C_6$ alkane. In some instances, gaseous alkane input streams may include only $C_2$ alkanes, only $C_3$ alkanes, only $C_4$ alkanes, only $C_5$ alkanes, or only $C_6$ alkanes. In some instances, gaseous alkane input streams may include a mixture of $C_2$-$C_5$ alkanes; a mixture of $C_3$-$C_6$ alkanes; a mixture of $C_2$-$C_4$ alkanes; a mixture of $C_3$-$C_5$ alkanes; a mixture of $C_4$-$C_6$ alkanes; a mixture of $C_2$ and $C_3$ alkanes; a mixture of $C_3$ and $C_4$ alkanes; a mixture of $C_4$ and $C_5$ alkanes; or a mixture of $C_5$ and $C_6$ alkanes. Example alkanes may include, but are not limited to, ethane, propane, n-butane, n-pentane, and n-hexane.

In some instances, gaseous alkane stream input may also contain $CH_4$ as an alkane component. $CH_4$ may or may not react with the metal sulfide depending on the operating conditions.

In some instances, gaseous alkane input streams may also include one or more non-alkane components, such as inert components. Example non-alkane components that may be present in gaseous alkane input streams include, but are not limited to, hydrogen ($H_2$), nitrogen ($N_2$) and argon (Ar).

Example sulfur streams may include one or more allotropes of sulfur. For instance, exemplary sulfur streams may include, but are not limited to, $S_2$, $S_3$, $S_4$, and $S_5$. In some instances, example sulfur streams may include hydrogen sulfide ($H_2S$) and/or mercaptans like $CH_3SH$. In some instances, example sulfur streams may include one or more inert carrier gases including, but not limited to, nitrogen ($N_2$) and argon (Ar).

In single reactor configurations, example reactors may also receive inert gas streams. Example inert gas streams may include, but are not limited to, nitrogen ($N_2$) and/or argon (Ar).

B. Output Streams

Exemplary reactor systems may generate various output streams. In two reactor configurations, one reactor may provide an output stream including one or more desired products and the other reactor may provide a second output stream.

Exemplary output streams may include one or more desired products. For instance, a metal sulfide ($MS_x$) particle reacting with an alkane in the gaseous alkane input stream may generate an alkene, a reduced metal sulfide ($MS_{x-1}$), and one or more of: hydrogen sulfide ($H_2S$) and other sulfur containing products like $S_2$, among other products. In single reactor and two reactor configurations, a product stream may include the generated alkene and one or more of hydrogen sulfide ($H_2S$) and other sulfur containing products, among other products. In two reactor configurations, the reduced metal sulfide ($MS_{x-1}$) may be provided to the other reactor.

As another example, a reduced metal sulfide ($MS_{x-1}$) particle reacting with sulfur in a sulfur stream may generate a metal sulfide ($MS_x$) particle. In some instances, a reactor output stream can include the generated hydrogen ($H_2$) when the input sulfur stream to the reactor contains a hydrogen feed such as $H_2S$. In some instances, a reactor output stream may include hydrogen sulfide ($H_2S$). In two reactor configurations, the metal sulfide ($MS_x$) particle may be provided to the first reactor.

C. Reactions

Various reactions may occur in exemplary reactor systems. For example, alkane(s) and metal sulfide ($MS_x$) may be provided to a reactor. The metal sulfide $MS_x$ may be capable of donating its sulfur to $H_2$ to form $H_2S$ and alkene(s). In this process, $MS_x$ converts to $MS_{x-1}$, which may be sent to a second reactor (or which may remain in the reactor in single reactor configurations). An input stream that includes sulfur may be used to regenerate the $MS_{x-1}$ to $MS_x$, where the $MS_{x-1}$ reacts with sulfur in the input stream to form $MS_x$.

Exemplary reactions are provided below without limitation. In implementations where propane is provided as an alkane, reaction (3) may occur in a reactor that includes a metal sulfide ($MS_x$) particle.

$$C_3H_8 + MS_x \rightarrow C_3H_6 + H_2S + MS_{x-1} \qquad (3)$$

In implementations where a reactor includes a reduced metal sulfide ($MS_{x-1}$) particle and receives a sulfur stream that includes $H_2S$, reaction (4) may occur:

$$MS_{x-1} + H_2S \rightarrow H_2 + MS_x \qquad (4)$$

In implementations where butane is provided as an alkane, reaction (5) may occur in a reactor that includes a metal sulfide ($MS_x$) particle.

$$C_4H_{10} + MS_x \rightarrow C_4H_8 + H_2S + MS_{x-1} \qquad (5)$$

In implementations where a reactor includes a reduced metal sulfide ($MS_{x-1}$) particle and receives a sulfur stream that includes $S_8$, reaction (6) may occur:

$$MS_{x-1} + (1/8)S_8 \rightarrow MS_x \qquad (6)$$

D. Metal Sulfide Particles

Various types of metal sulfide particles may be utilized in exemplary systems and methods. Generally, metal sulfide particles used in exemplary systems and methods are either in a reduced form or in an oxidized form. The reduced or oxidized terms refer to the change in oxidation state of the metal, lattice sulfur species, or both. Oxidized metal sulfide particles can react with an alkane, dehydrogenate the alkane, and form $H_2S$, which reduces the oxidized metal sulfide particle into a reduced metal sulfide or a metal/metal alloy.

The reduced metal sulfide particle or metal/metal alloy can accept sulfur in the solid lattice from a sulfur source. Upon sulfur addition/oxidation, reduced metal sulfide particles can form oxidized metal sulfide particles.

Exemplary metal sulfide particles have an active metal capable of forming sulfides where active metal, sulfur, or both display one or more than one oxidation states. Generally, example metals (M) may be transition state, metalloid, or rare earth metals. In some instances, example metal sulfide particles may be bimetallic or trimetallic. Example metals (M) include, but are not limited to, Fe, Co, Ni, Cu, W, La, Ce, Ti, Zn, Cd, Ru, Rh, and Pb. The metals may include sulfide ($S^{2-}$), persulfide ($S_2^{2-}$), or another sulfur species.

There may be more than one active metal in a metal sulfide either in the form of a mixed metal sulfide or as a promotor or dopant. Dopants and promoters may be alkali metals, alkaline earth metals, transition state metals, metalloid metals, or rare earth metals. Supports may be inert oxides of alkali metals, sulfides of alkali metals, alkaline earth metals, transition state metals, metalloid metals, or rare earth metals. The amount of support, promoter, or dopant material may vary from 0.01 wt %, 10 wt %, 20 wt %, 30 wt % 40 wt %, 50 wt %, 60 wt %, 70 wt %, 80 wt %, 90 wt % or any value in between.

The metal sulfide may contain metal sulfides from group I or group II in the form of promotor, dopant, or to form mixed metal sulfides. Inert sulfides such as, but not limited to $MoS_2$, $Ce_2S_3$, MgS, $Na_2S$ may be used as supports and dopants and promotors as well. Inert oxides that do not react with the metal sulfide may be used as promotor, dopant, or as a support. Examples of promotors, dopants, or supports may include, but not limited to, $K_2O$, MgO, $SiO_2$, and $Al_2O_3$, as well as mixed metal oxides such as Mg $Al_2O_4$.

Oxides that do react with the sulfide to form metastable structures can also be considered as a metal sulfide. Dopants, promoters, and supports, in addition to other components, may provide high surface area, highly active sulfur vacancies.

Exemplary metal sulfide particles may be synthesized by any suitable method including, but not limited to, wet milling, extrusion, pelletizing, freeze granulation, co-precipitation, wet-impregnation, sol-gel, and mechanical compression. Certain techniques may be used to increase the strength and/or reactivity of exemplary metal sulfide particles, such as sintering synthesized particles or adding a binder or sacrificial agent with synthesis methods such as sol-gel combustion.

Exemplary metal sulfide particles may be provided as powders or pellets. Example powders may include metal sulfide particles having a size of about 100 μm. Example pellets may include metal sulfide particles having a size of about 2 mm.

Example metal sulfide particles may be bulk structures or mesoporous supported nanoparticles. Example bulk structures may have random orientations of large grains, cage-like structures for added physical strength, layered structure, or similar configurations. Example mesoporous supported metal sulfide particles may have a mesoporous support such as Santa Barbara Amorphous-15 silica (SBA-15), Santa Barbara Amorphous-16 silica (SBA-16), and other SBA variants, Mesoporous-$Al_2O_3$, Mesoporous $CeO_2$, etc., which have micro and meso pores, in which metal sulfide nanoparticles may be embedded.

Example metal sulfide particles may have various densities. For instance, example metal sulfide particles may have a density of from 1.5 $g/cm^3$ to 6 $g/cm^3$. In various implementations, example metal sulfide particles may have a density of from 1.5 $g/cm^3$ to 3 $g/cm^3$; 3 $g/cm^3$ to 6 $g/cm^3$; 2 $g/cm^3$ to 4 $g/cm^3$; 4 $g/cm^3$ to 6 $g/cm^3$; 1.5 $g/cm^3$ to 2 $g/cm^3$; 2 $g/cm^3$ to 3 $g/cm^3$; 3 $g/cm^3$ to 4 $g/cm^3$; 4 $g/cm^3$ to 5 $g/cm^3$; or 5 $g/cm^3$ to 6 $g/cm^3$.

II. REACTOR CONFIGURATIONS AND OPERATING CONDITIONS

Exemplary reactor systems may be single reactor system configurations or two reactor system configurations. In single reactor system configurations, example reactors may be configured to be fixed bed reactors. In two reactor system configurations, example reactors may be configured to be moving beds, ebullated beds, fluidized beds, or combinations thereof.

Exemplary reactor systems disclosed and characterized herein can operate under temperatures and pressures sufficient for alkene generation and metal sulfide regeneration.

Temperatures within exemplary reactors during oxidative dehydrogenation (performed in the first reactor in two reactor systems) are typically between 200° C. and 1200° C. In various implementations, a temperature of an exemplary reactor during oxidative dehydrogenation can be between 300° C. to 1100° C.; 400° C. to 1000° C.; 200° C. to 500° C.; 500° C. to 800° C.; 800° C. to 1100° C.; 400° C. to 800° C.; 800° C. to 1200° C.; 500° C. to 700° C.; 700° C. to 900° C.; 900° C. to 1100° C.; 600° C. to 800° C.; 400° C. to 500° C.; 500° C. to 600° C.; 600° C. to 700° C.; 700° C. to 800° C.; 800° C. to 900° C.; or 900° C. to 1000° C.

Temperatures within exemplary reactors during sulfidation (performed in the second reactor in two reactor systems) are typically between 200° C. and 1000° C. In various implementations, a temperature of an exemplary reactor during sulfidation can be between 300° C. to 900° C.; 400° C. to 800° C.; 200° C. to 600° C.; 600° C. to 1000° C.; 300° C. to 500° C.; 500° C. to 700° C.; 700° C. to 925° C.; 300° C. to 400° C.; 400° C. to 500° C.; 500° C. to 600° C.; 600° C. to 700° C.; 700° C. to 800° C.; or 800° C. to 1000° C.

Pressures within exemplary reactors during oxidative dehydrogenation (performed in the first reactor in two reactor systems) are typically between 1 atm and 30 atm. In various implementations, a pressure of an exemplary reactor during oxidative dehydrogenation can be between 1 atm and 15 atm; 15 atm and 30 atm; 2 atm and 25 atm; 5 atm and 20 atm; 1 atm and 5 atm; 5 atm and 10 atm; 10 atm and 15 atm; 15 atm and 20 atm; 20 atm and 25 atm; 25 atm and 30 atm; 1 atm and 3 atm; 3 atm and 6 atm; 6 atm and 9 atm; 9 atm and 12 atm; 1 atm and 2 atm; 2 atm and 3 atm; 3 atm and 4 atm; 4 atm and 5 atm; 5 atm and 6 atm; 6 atm and 7 atm; 7 atm and 8 atm; 8 atm and 9 atm; or 9 atm and 10 atm.

Pressures within exemplary reactors during sulfidation (performed in the second reactor in two reactor systems) are typically between 1 atm and 30 atm. In various implementations, a pressure of an exemplary reactor during sulfidation can be between 1 atm and 15 atm; 15 atm and 30 atm; 2 atm and 25 atm; 5 atm and 20 atm; 1 atm and 5 atm; 5 atm and 10 atm; 10 atm and 15 atm; 15 atm and 20 atm; 20 atm and 25 atm; 25 atm and 30 atm; 1 atm and 3 atm; 3 atm and 6 atm; 6 atm and 9 atm; 9 atm and 12 atm; 1 atm and 2 atm; 2 atm and 3 atm; 3 atm and 4 atm; 4 atm and 5 atm; 5 atm and 6 atm; 6 atm and 7 atm; 7 atm and 8 atm; 8 atm and 9 atm; or 9 atm and 10 atm.

Various flow rates may be used within exemplary reactors during oxidative dehydrogenation (performed in the first reactor in two reactor systems) and sulfidation (performed in the second reactor in two reactor systems). Specific flow rates can vary, particularly depending upon the scale of the operation, based on the stoichiometry and reaction kinetics of particular alkane and $MS_x$ pairs or sulfur-containing MS pairs. For illustration, example gas hourly space velocities can vary from 1 ml/g·hr to 5000 ml/g·hr.

For the single reactor configuration, the temperature, pressure and gas hourly space velocities mentioned for the two-reactor system are applicable.

For the single reactor configuration, the outlet gas composition may be measured or estimated to determine the segment times of the alkane dehydrogenation step or the sulfidation step.

The threshold value for the alkane dehydrogenation step may be determined by the conversion of the alkane, selectivity of the desired alkene, $H_2S$/Sulfur containing compounds produced or a combination of these parameters.

The threshold value for the inert purging step may be determined by the volume of the reactor. The time for this segment can be determined by sending the inert gas into the reactor where the volume of the gas inside the reactor is replaced by anywhere between 2 to 10 times to ensure the gas has been purged.

The threshold value for the sulfidation step is determined by the amount of sulfur that reacted with the reduced metal sulfide. This may be estimated by measuring the difference between the sulfur in the inlet and outlet streams through gas analyzers.

III. SYSTEM ARRANGEMENTS

Figure 2:
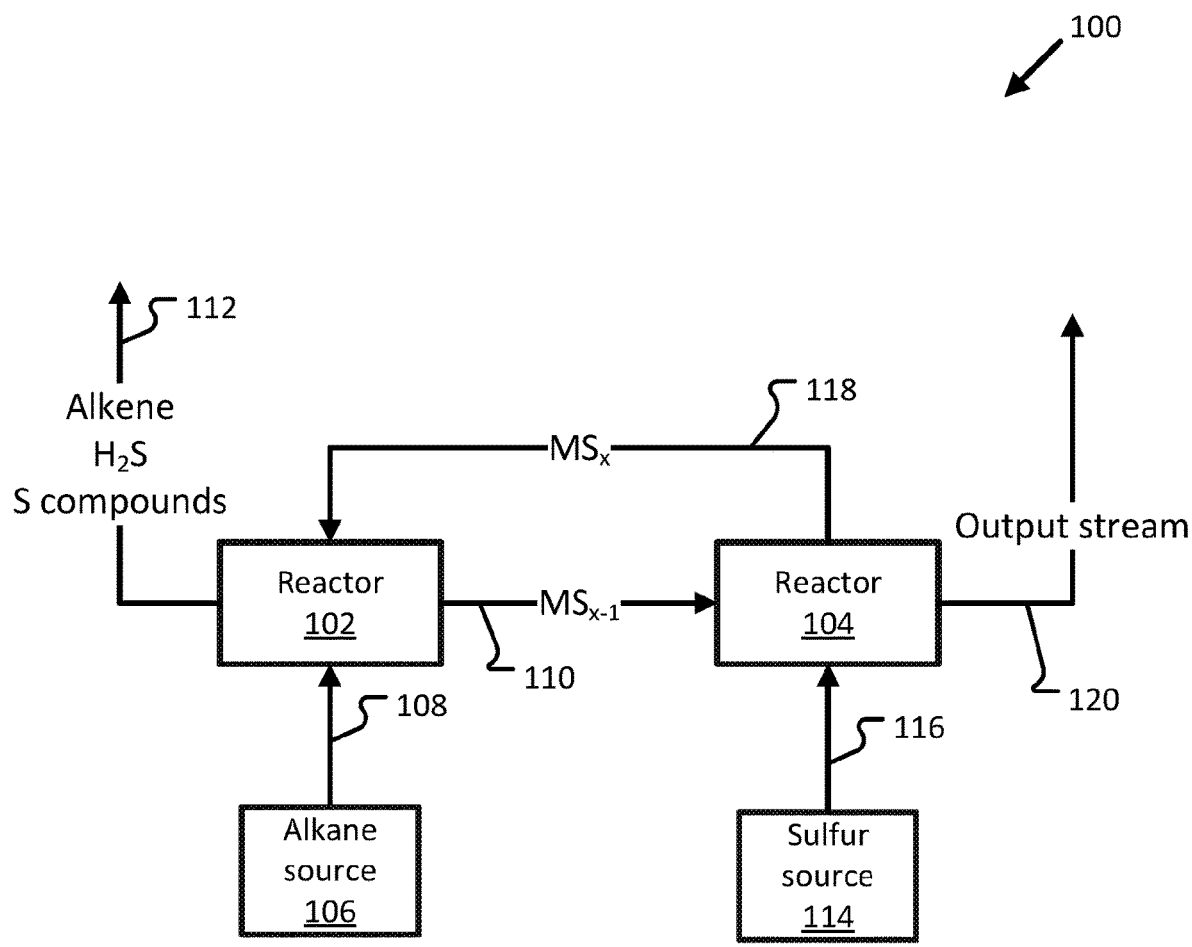
FIG. 2 is a schematic diagram showing an exemplary two reactor system for generating alkenes.

FIG. 2 shows a schematic diagram of an exemplary reactor system 100. As shown, reactor system 100 includes reactor 102, reactor 104, alkane source 106, and sulfur source 114. Reactor system 100 is an example embodiment of a two reactor system that may be used for alkene generation using metal sulfides. Reactor system 100 may be configured for continuous operation. Other embodiments may include more or fewer components.

Reactor 102 receives gaseous alkane input stream 108 and metal sulfide ($MS_x$) particles via input 118. The metal sulfide ($MS_x$) particles react with alkane from gaseous alkane input stream 108 to generate an alkene, a reduced metal sulfide ($MS_{x-1}$) particle, hydrogen sulfide ($H_2S$) and other sulfur containing streams formed during the reaction. The reduced metal sulfide ($MS_{x-1}$) particles are provided to reactor 104 via input 110.

Alkane source 106 provides one or more alkanes to reactor 102 in gaseous alkane input stream 108. Alkane source 106 may be configured to adjust a flow rate of gaseous alkane input stream 108. In some instances, the flow rate of gaseous alkane input stream 108 may be adjusted based on conversion data for an output stream 112 of reactor 102.

Reactor 102 provides a product stream 112 that includes alkene and hydrogen sulfide $H_2S$). Product stream 112 can also include one or more sulfur-containing compounds. In some instances, product stream 112 includes one or more monitoring units to monitor conversion rates in reactor 102. Based on measured conversion rates, flow rates of the gaseous alkane input stream 108 and/or metal sulfide particles ($MS_x$) may be adjusted to achieve desired conversion rates.

Reactor 104 may receive a sulfur stream 116 from sulfur source 114 and reduced metal sulfide ($MS_{x-1}$) particles 110 from reactor 110. In reactor 104, the reduced metal sulfide ($MS_{x-1}$) particles may react with sulfur in the sulfur stream to generate the metal sulfide ($MS_x$) particle and hydrogen ($H_2$). One or more additional components may be generated depending upon constituents in sulfur stream 116.

Sulfur source 114 provides a sulfur stream 116 to reactor 104. Sulfur source 114 may be configured to adjust a flow rate of sulfur stream 116. In some instances, the flow rate of sulfur stream 116 may be adjusted based on conversion data for an output stream 120 of reactor 104. In various implementations, and as discussed in greater detail above, sulfur stream 116 may include one or more allotrope of sulfur and/or hydrogen sulfide ($H_2S$).

Reactor 104 provides metal sulfide ($MS_x$) particles to reactor 102. Reactor 104 also provides an output stream 120 that includes one or more gaseous components. For instance, output stream 120 can include hydrogen ($H_2$).

Output stream 120 may include hydrogen sulfide ($H_2S$). In some instances, reactor system 100 may also include one or more separation units (not shown in FIG. 2) that can separate hydrogen sulfide ($H_2S$) from output stream 120. Then, the separated hydrogen sulfide ($H_2S$) may be recycled to reactor 104.

In some instances, reactor system 100 may include one or more separation units (not shown in FIG. 2) that can separate hydrogen sulfide ($H_2S$) from product stream 112 generated by reactor 102. Then, the separated hydrogen sulfide ($H_2S$) may be recycled to reactor 104.

Figure 3:
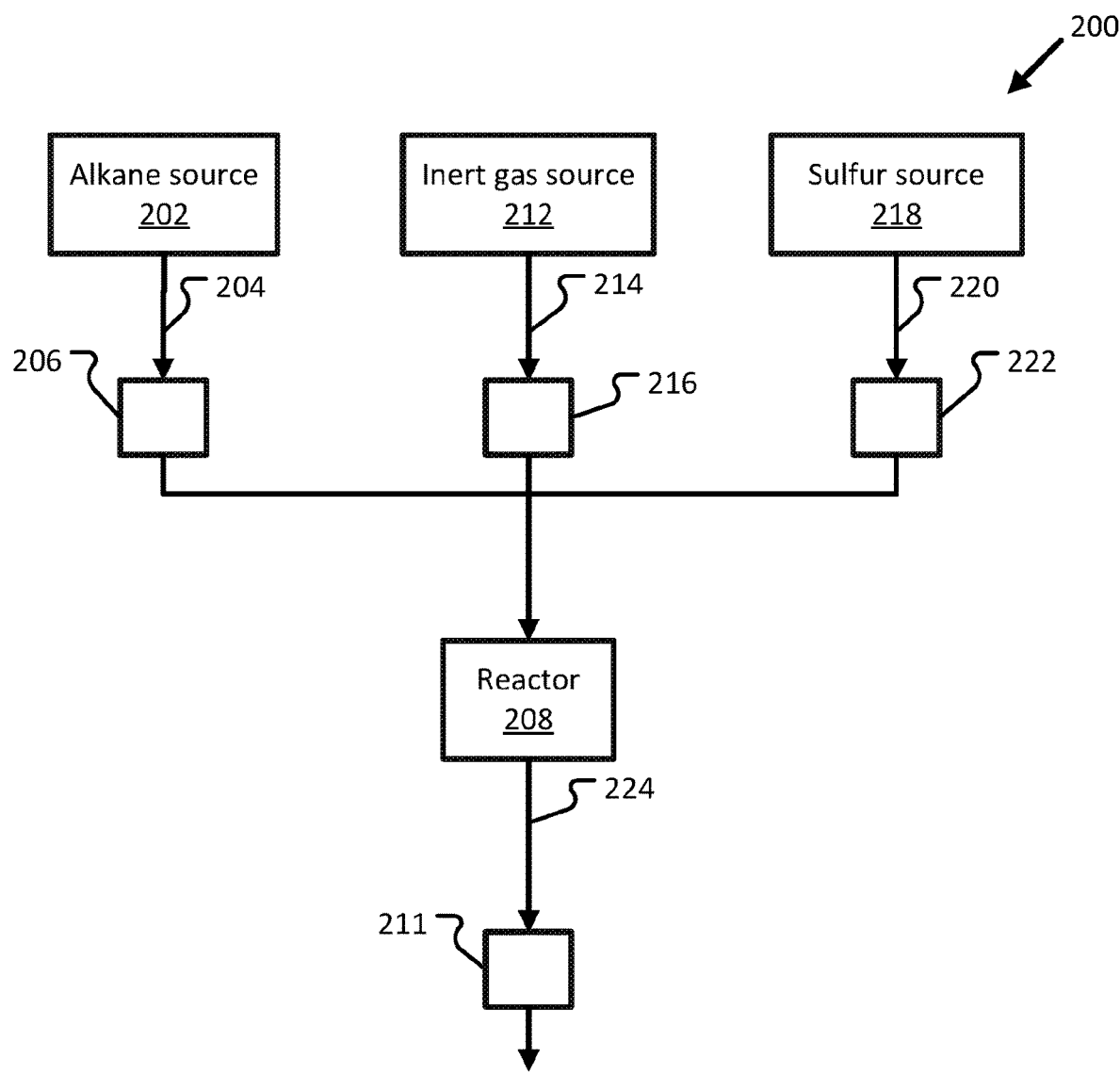
FIG. 3 is a schematic diagram showing an exemplary single reactor system for generating alkenes.

FIG. 3 shows a schematic diagram of example reactor system 200. As shown, reactor system 200 includes reactor 208, alkane source 202, inert gas source 212, and sulfur source 218. Reactor system 200 is an exemplary embodiment of a single reactor system that may be used for alkene generation using metal sulfides. Reactor system 200 may be configured for batch operation. Other embodiments may include more or fewer components.

Alkane source 202 may provide a gaseous alkane input stream 204 to reactor 208. One or more flow regulation units 206 may be used to selectively provide gaseous alkane input stream 204 to reactor 208 and/or control a flow rate of gaseous alkane input stream 204. Exemplary components that may be included in gaseous alkane input stream 204 are discussed in greater detail above.

Reactor 208 may be configured as a fixed bed reactor including metal sulfide ($MS_x$) particles. In reactor 208, the metal sulfide ($MS_x$) particles may react with alkane in gaseous alkane input stream 204 to generate an alkene, a reduced metal sulfide ($MS_{x-1}$) particle, and hydrogen sulfide ($H_2S$).

Reactor 208 may generate a product stream 224 that includes alkene and hydrogen sulfide ($H_2S$), and, in some instances, sulfur-containing compounds. Gas analyzer unit 211 may monitor alkane conversion and/or alkene selectivity. One or both of those values can be compared to a threshold value and, upon reaching the value, flow regulation unit 206 may stop the flow of gaseous alkane input stream 204 to reactor 208.

Inert gas source 212 may provide an inert gas stream 214 to reactor 208. One or more flow regulation units 216 may be used to selectively provide inert gas stream 214 to reactor 208 and/or control a flow rate of inert gas stream 214. Exemplary components of inert gas stream 214 are discussed in greater detail above. Generally, inert gas stream 214 can purge alkane(s), $H_2S$, and alkene gas from reactor 208.

Gas analyzer unit 211 may monitor alkane(s), $H_2S$, and alkene gas content in output stream 224. Upon detecting that most or all of those components are not present in output stream 224, flow regulation unit 216 may be configured to stop a flow of inert gas stream 214.

Sulfur source 218 may provide a sulfur stream 220 to reactor 208. One or more flow regulation units 222 may be used to selectively provide sulfur stream 220 to reactor 208 and/or control a flow rate of sulfur stream 220. Example components of sulfur stream 220 are discussed in greater detail above.

Gas analyzer unit 211 may be used to monitor hydrogen ($H_2$) content in output stream 224. Upon detecting a desired conversion of metal sulfide, flow regulation unit 222 may be configured to stop a flow of sulfur stream 220. Another purge of reactor 208 can be subsequently run by providing the inert gas stream 214 to reactor 208.

Usually, reactor 208 receives only one of gaseous alkane input stream 204, inert gas stream 214, and sulfur stream 220 at a time. That is, those streams are usually not mixed together and provided to reactor 208.

IV. METHODS OF OPERATION

Figure 4:
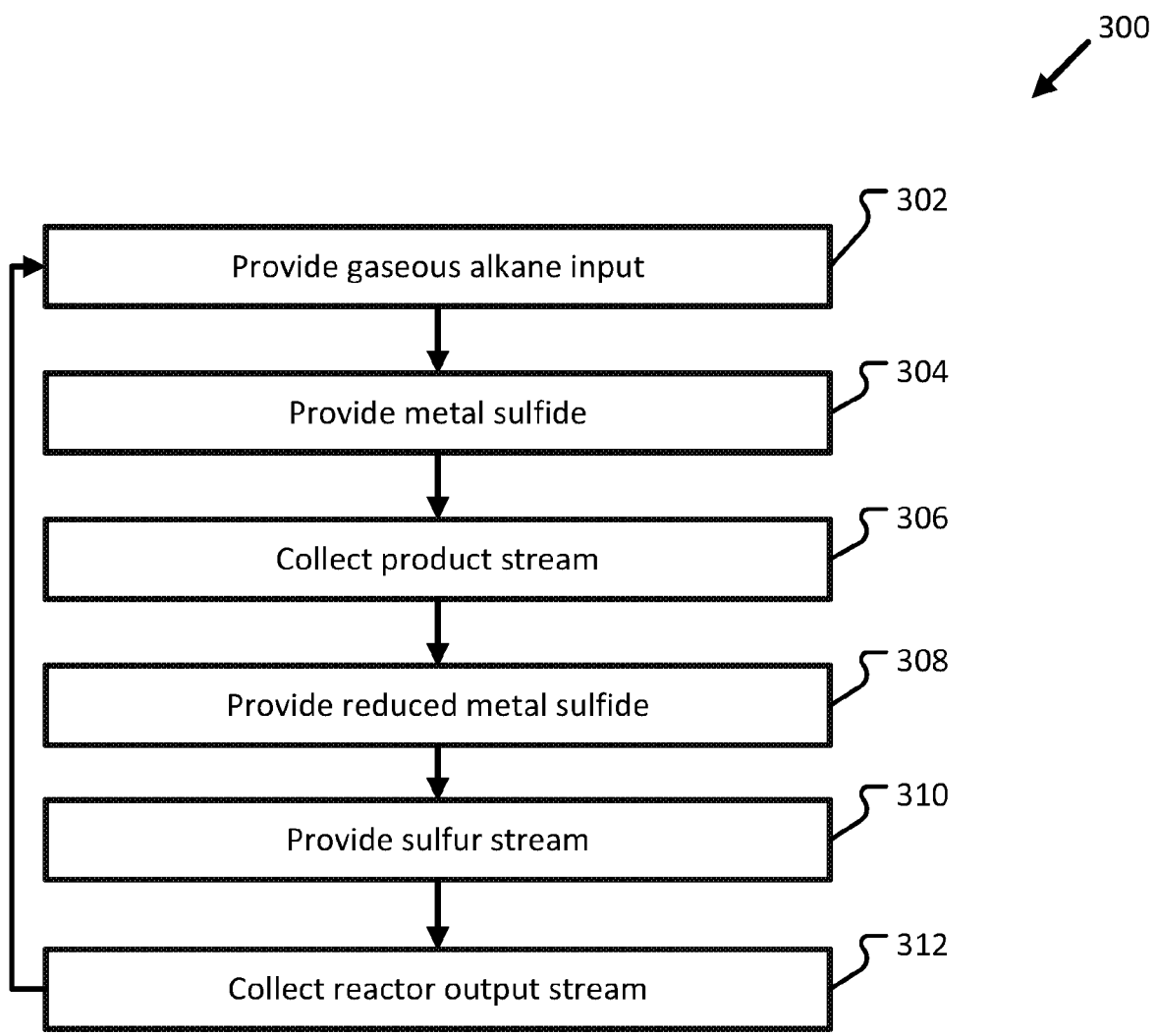
FIG. 4 is a schematic diagram of an exemplary method for operating the two reactor system shown in FIG. 2.

FIG. 4 shows example method 300 for operating a reactor system. In some instances, method 300 may be used to operate example two reactor system 100 discussed above with reference to FIG. 2. Other embodiments of method 300 may include more or fewer operations.

Method 300 may begin by providing a gaseous alkane input stream (operation 302) to a first reactor. The alkane in the gaseous alkane input stream may include at least one $C_2$-$C_6$ alkane. Other aspects of the gaseous alkane input stream are discussed in greater detail above.

Metal sulfide ($MS_x$) particles also may be provided (operation 304) to the first reactor. Various aspects of exemplary metal sulfide ($MS_x$) particles are discussed in greater detail above. In the first reactor, the metal sulfide ($MS_x$) particles may react with alkane in the gaseous alkane input stream to generate an alkene, reduced metal sulfide ($MS_{x-1}$) particles, and hydrogen sulfide $H_2S$) and/or one or more other sulfur containing compounds.

In some instances, during operation, a temperature of the first reactor may be maintained to be between 200° C. and 1200° C. In some instances, during operation, a pressure of the first reactor may be maintained to be between 1 atm and 30 atm.

During operation, a product stream may be collected (operation 306) from the first reactor. Typically, the product stream includes the alkene generated in the first reactor and hydrogen sulfide ($H_2S$). In some instances, exemplary method 300 may also include separating the hydrogen sulfide ($H_2S$) from the product stream and recycling the separated hydrogen sulfide ($H_2S$) to the second reactor.

The reduced metal sulfide ($MS_{x-1}$) particles may be provided (operation 308) to the second reactor. A sulfur stream also may be provided to the second reactor (operation 310). Various aspects of example sulfur streams, including example components, are discussed above in greater detail. In the second reactor, the reduced metal sulfide ($MS_{x-1}$) particle reacts with sulfur in the sulfur stream to generate the metal sulfide ($MS_x$) particle and hydrogen ($H_2$).

A second reactor output stream may be collected (operation 312). The second reactor output stream may include, at least, hydrogen ($H_2$). In some instances, the second reactor output stream may include hydrogen sulfide ($H_2S$). Optionally, example method 300 may include separating the hydrogen sulfide ($H_2S$) from the second reactor output stream and recycling the separated hydrogen sulfide ($H_2S$) to the second reactor.

Figure 5:
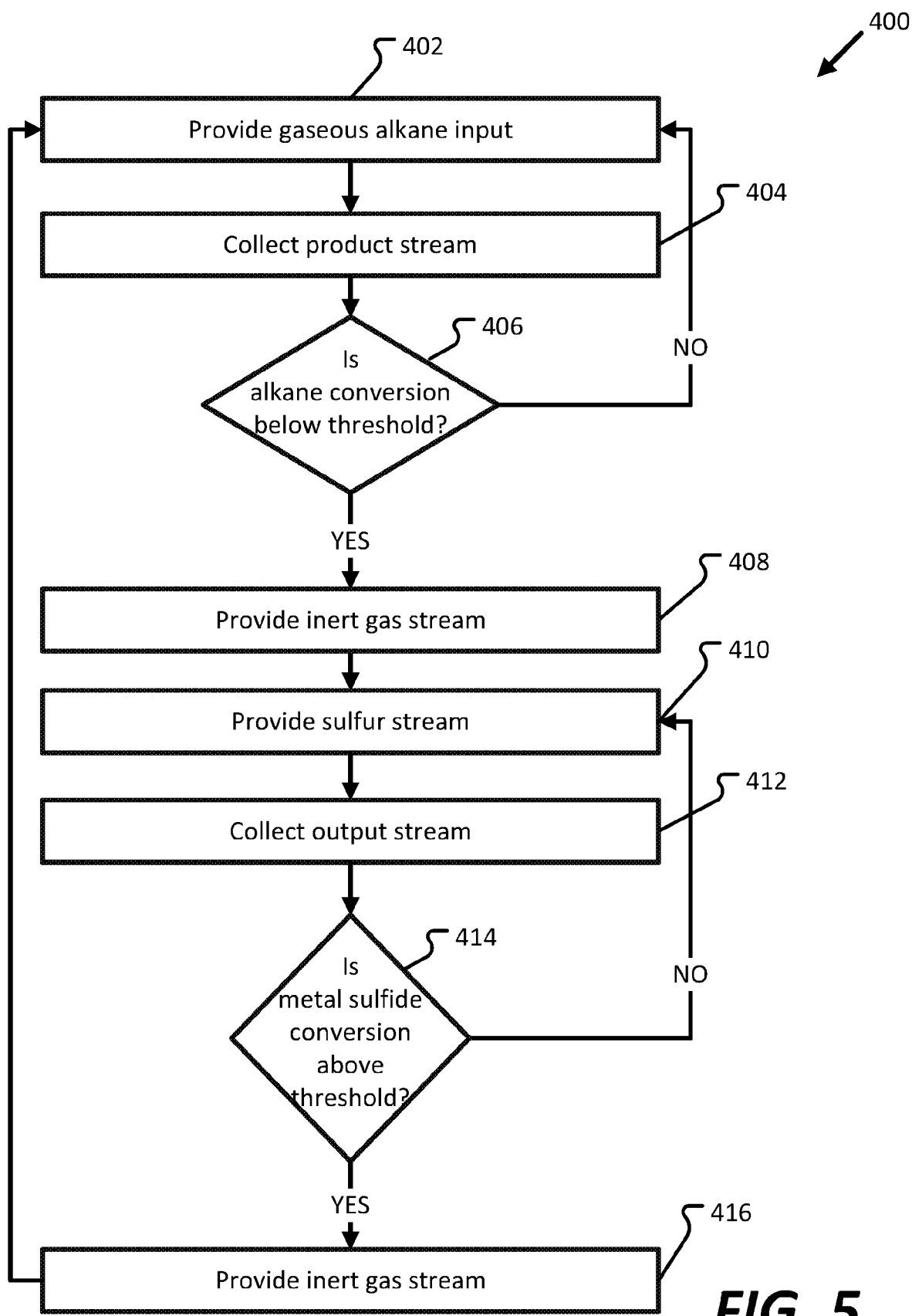
FIG. 5 is a schematic diagram showing an exemplary method for operating the single reactor system shown in FIG. 3.

FIG. 5 shows exemplary method 400 for operating a reactor system. In some instances, method 400 can be used to operate a single reactor system 200 discussed above with reference to FIG. 3. Typically, exemplary method 400 is performed with a fixed bed reactor that includes metal sulfide ($MS_x$) particles. Other embodiments of method 400 may include more or fewer operations.

Method 400 may begin by providing a gaseous alkane input stream (operation 402) to the reactor. The alkane in the gaseous alkane input stream may include at least one $C_2$-$C_6$ alkane. Other aspects of the gaseous alkane input stream are discussed in greater detail above. The metal sulfide ($MS_x$) particles react with alkane in the gaseous alkane input stream to generate an alkene, a reduced metal sulfide ($MS_{x-1}$) particle, and hydrogen sulfide ($H_2S$). A product stream is collected (operation 404) that includes, at least, the alkene and hydrogen sulfide ($H_2S$) and/or one or more other sulfur-containing compounds.

While providing the gaseous alkane input stream, the product stream can be monitored for whether alkane conversion is below a predetermined threshold (operation 406). If alkane conversion is above the predetermined threshold, the gaseous alkane input stream may be continually provided (operation 402) to the reactor. In some instances, while providing the gaseous alkane input stream (operation 402), a temperature of the reactor may be maintained to be between 200° C. and 1200° C. and a pressure of the reactor can be maintained to be between 1 atm and 30 atm.

If alkane conversion is below the predetermined threshold, then the gaseous alkane input stream may be stopped, and an inert gas stream is provided (operation 408) to the reactor. Providing the inert gas stream can purge alkane, alkene, and $H_2S$ from the reactor. In some instances, a reactor output stream may be monitored, and inert gas may be provided until alkane, alkene, and/or $H_2S$ content drops below a predetermined threshold. In some instances, the hydrogen sulfide ($H_2S$) may be separated from the reactor output stream and recycled back to the reactor.

After providing the inert gas stream, a sulfur stream may be provided (operation 410) to the reactor. The sulfur stream may include one or more sulfur-containing components, such as an allotrope of sulfur or hydrogen sulfide ($H_2S$). Additional details about the sulfur stream are provided above. In some instances, while providing the sulfur stream (operation 410), a temperature of the reactor may be maintained to be between 200° C. and 1000° C. and a pressure of the reactor may be maintained to be between 1 atm and 30 atm.

After providing the sulfur stream (operation 410), the reduced metal sulfide ($MS_{x-1}$) particle may react with sulfur in the sulfur stream to generate the metal sulfide ($MS_x$) particle and hydrogen ($H_2$). The reactor output stream may be collected (operation 412), which includes, at least, hydrogen ($H_2$).

The reactor output stream may be monitored (operation 414) for whether metal sulfide conversion in the reactor is above a predetermined threshold. If the metal sulfide conversion is below the predetermined threshold, the sulfur stream may be continued to be provided (operation 410) to the reactor.

If the metal sulfide conversion is above the predetermined threshold, then sulfur stream may be stopped. Then, the inert gas stream may be provided (operation 416) to the reactor. Providing the inert gas stream can purge the reactor of gaseous species generated while sulfur was provided to the reactor. Then, method 400 may return to operation 402 and gaseous alkane input stream can be provided to the reactor.

V. EXPERIMENTAL EXAMPLES

Experimental examples were conducted, and various aspects are discussed below. In particular, two experiments were conducted where metal sulfide particles were iron (Fe)-based, propane was the alkane, and H₂S was the sulfur source.

A. Exemplary Fe—S System

Figure 6:
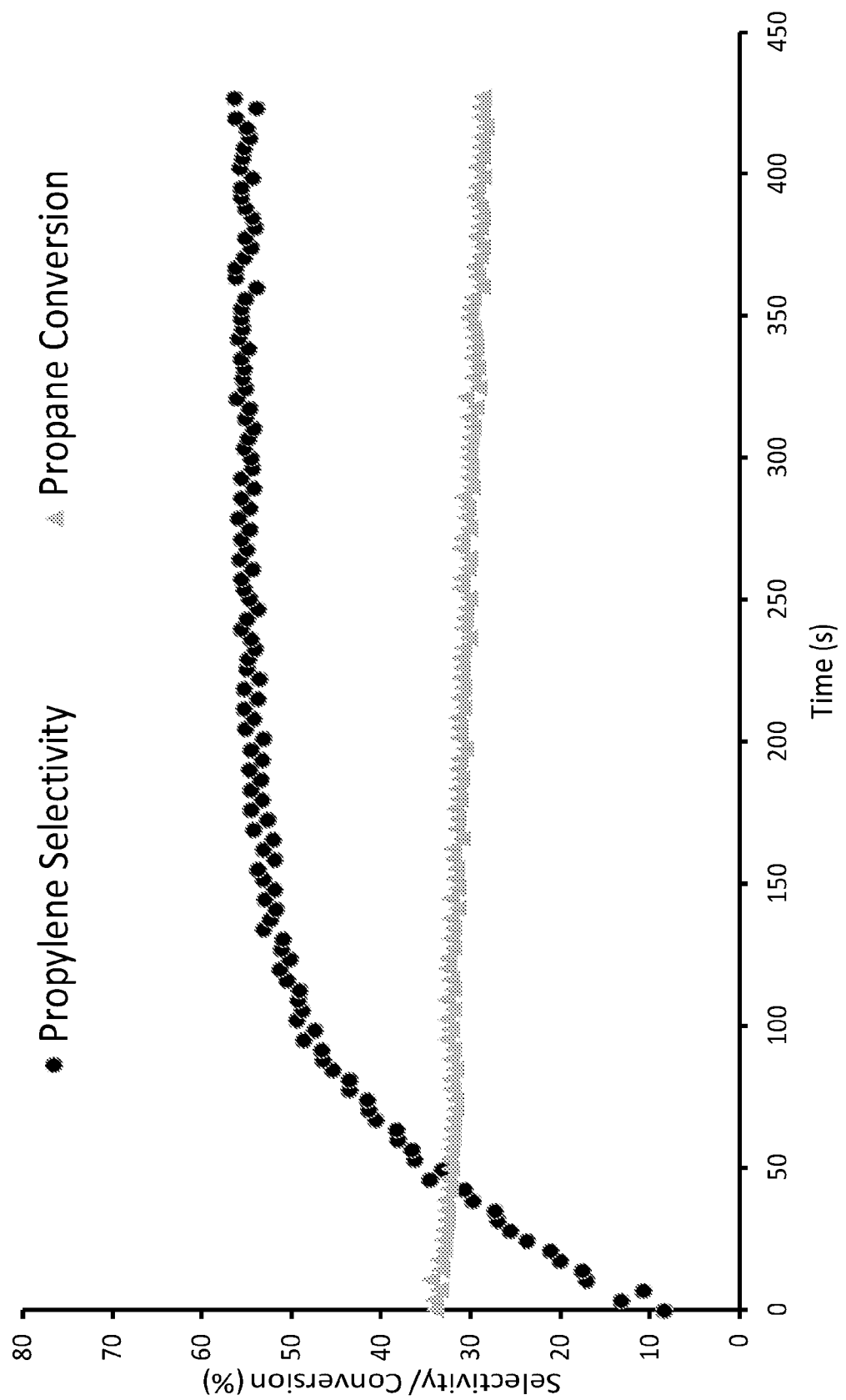
FIG. 6 is a graph showing experimental data for propane conversion and propylene selectivity values over time for an oxidative dehydrogenation reaction including propane, $H_2S$, and $Fe_{0.89}S$ at 650° C.
Figure 7:
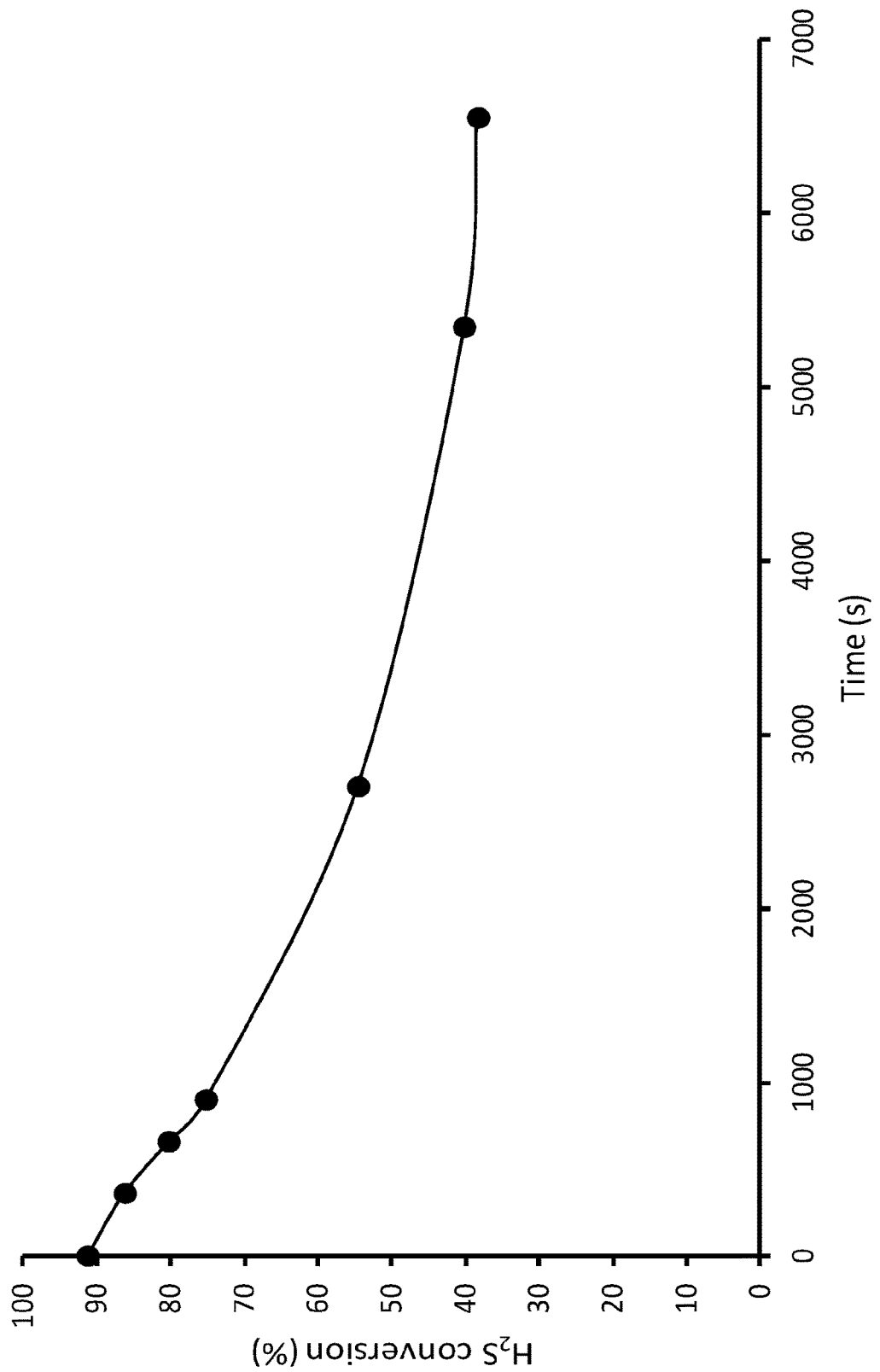
FIG. 7 is a graph showing experimental data for $H_2S$ conversion over time for the sulfidation reaction of FeS to form $Fe_{0.89}S$ at 850° C.

An example first reactor was operated at 650° C. with a propane space velocity of 300 ml/g·hr and $Fe_{0.89}S$ metal sulfide particles. An example second reactor was operated at 800° C. with an H₂S space velocity of 15 ml/g·hr. The reaction was carried out in a u-tube reactor and a mass spectrometer was used to measure the gas composition for the alkane dehydrogenation step. For the sulfidation step, a H₂S gas analyzer was used. The mass spectrometer and the H₂S analyzer were calibrated with known concentrations of gas mixtures. These continuous gas analyzers analyzed a slip stream of the product gas. Results for this example system are shown in FIG. 6 and FIG. 7. FIG. 6 shows data for the oxidative dehydrogenation reaction in the first reactor, and FIG. 7 shows an H₂S sulfidation reaction of FeS to $Fe_{0.89}S$.

A characteristic trend seen in FIG. 6 for propylene selectivity and propane conversion can be attributed to the change in the surface species with the reaction time. A maximum yield of propylene was calculated to be 17.2%. A loss in sulfur from the iron sulfide in the first reactor is seen in the form of H₂S production in gas phase along with the propylene produced. The sulfidation reaction converts H₂S into H₂, re-sulfating the iron sulfide into the original state of $Fe_{0.89}S$.

To measure the performance of metal sulfides, thermodynamic studies were conducted using H₂ as reactant gas. There are two ways in which alkanes can interact with metal sulfides in S—ODH reactor, alkanes react directly with metal sulfides to form alkenes and H₂S or alkanes can thermochemically crack over metal sulfide surface forming alkenes and H₂. This H₂ then reacts with metal sulfide to form H₂S. In both these ways, formation of H₂S drives the reaction and pushes dehydrogenation equilibrium forward. Hence, to assess metal sulfides for the proposed process, its ability to convert H₂ to H₂S should be measured as it is the equilibrium determining reaction. In view of this, all thermodynamic calculations on metal sulfides are performed with H₂ as reactant rather than any alkanes.

Figure 8:
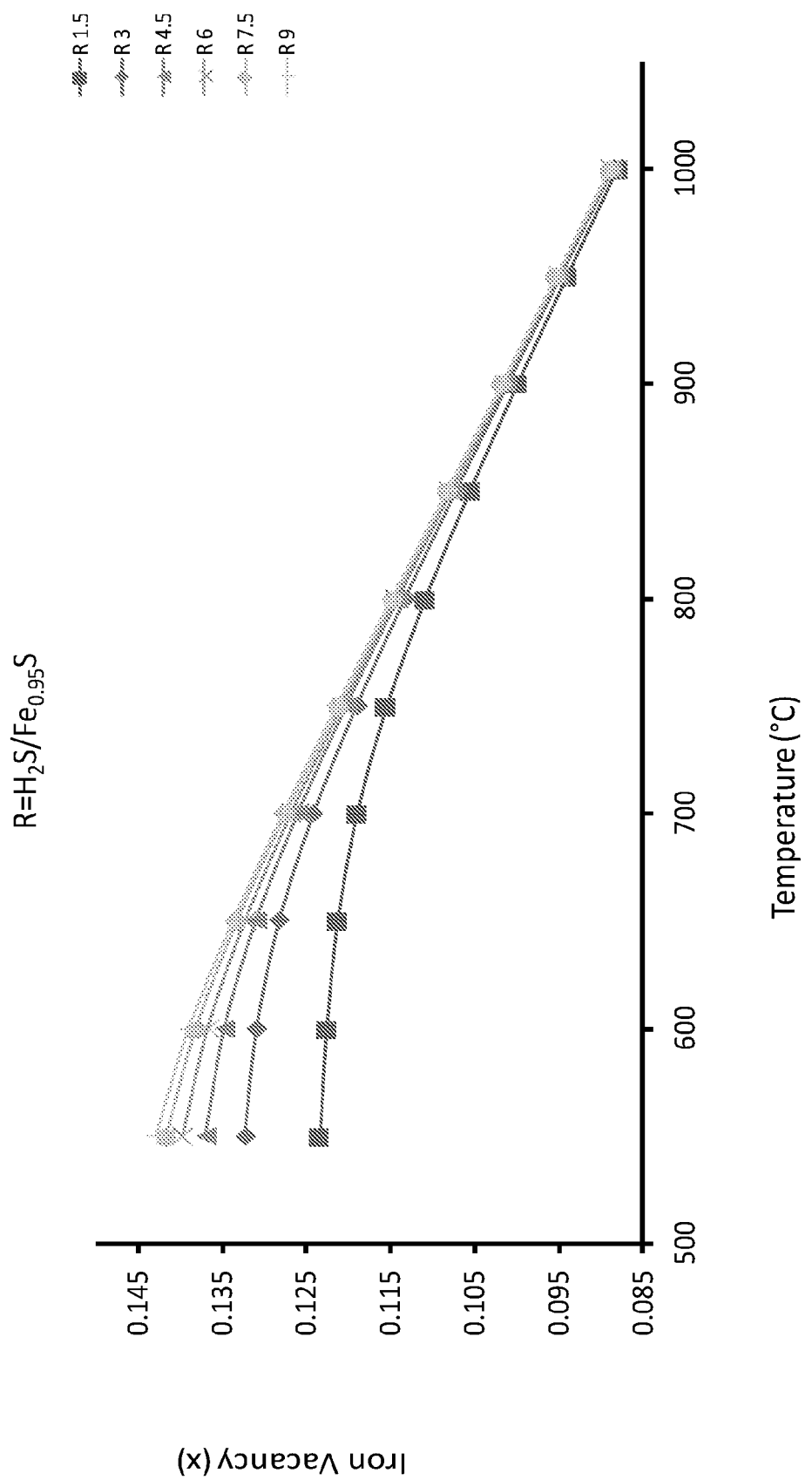
FIG. 8 is a graph showing experimental data for temperature dependence of iron vacancy in Fe—S system for a sulfidation reaction.
Figure 9:
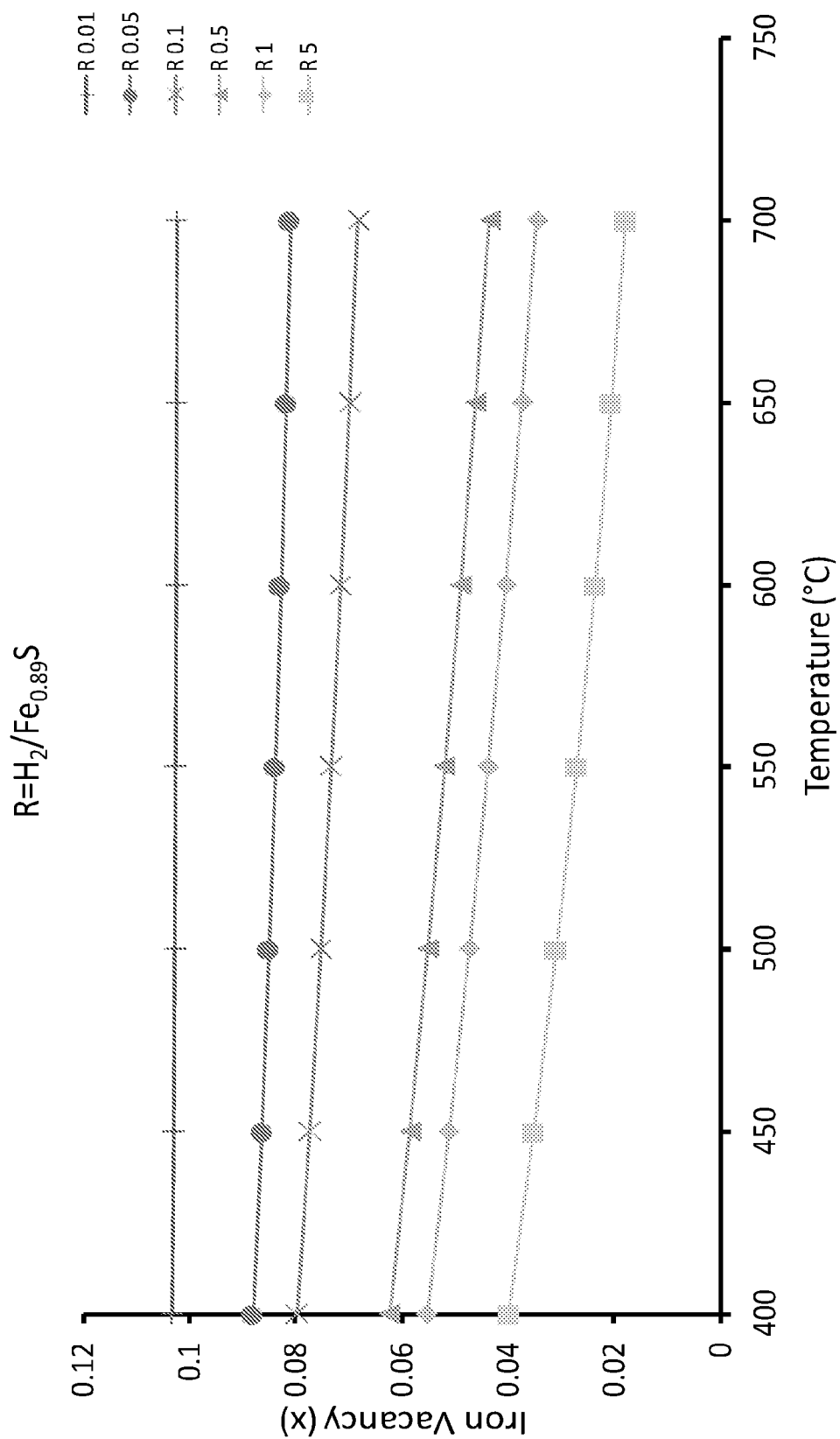
FIG. 9 is a graph showing experimental data for temperature dependence of iron vacancy in Fe—S system for an oxidative dehydrogenation reaction, assuming $H_2$ to be the reactive species from alkane dehydrogenation.

Generally, FIG. 8 and FIG. 9 show thermodynamic data for the Fe—S system. FIG. 8 shows temperature dependence of iron (Fe) vacancy in the Fe—S system for the sulfidation reaction. FIG. 9 shows temperature dependence of iron (Fe) vacancy in the Fe—S system for the oxidative dehydrogenation reaction, assuming H₂ to be the reactive species from alkane dehydrogenation. Under the current reaction conditions and temperatures, the system favorably forms $Fe_{(1-x)}S$ or pyrrhotite phase, where x varies between 0 and 0.2. The vacancy 'x' directly correlates to the amount of sulfidation of a particular phase.

B. Exemplary Fe—S—SiO₂ System

Figure 10:
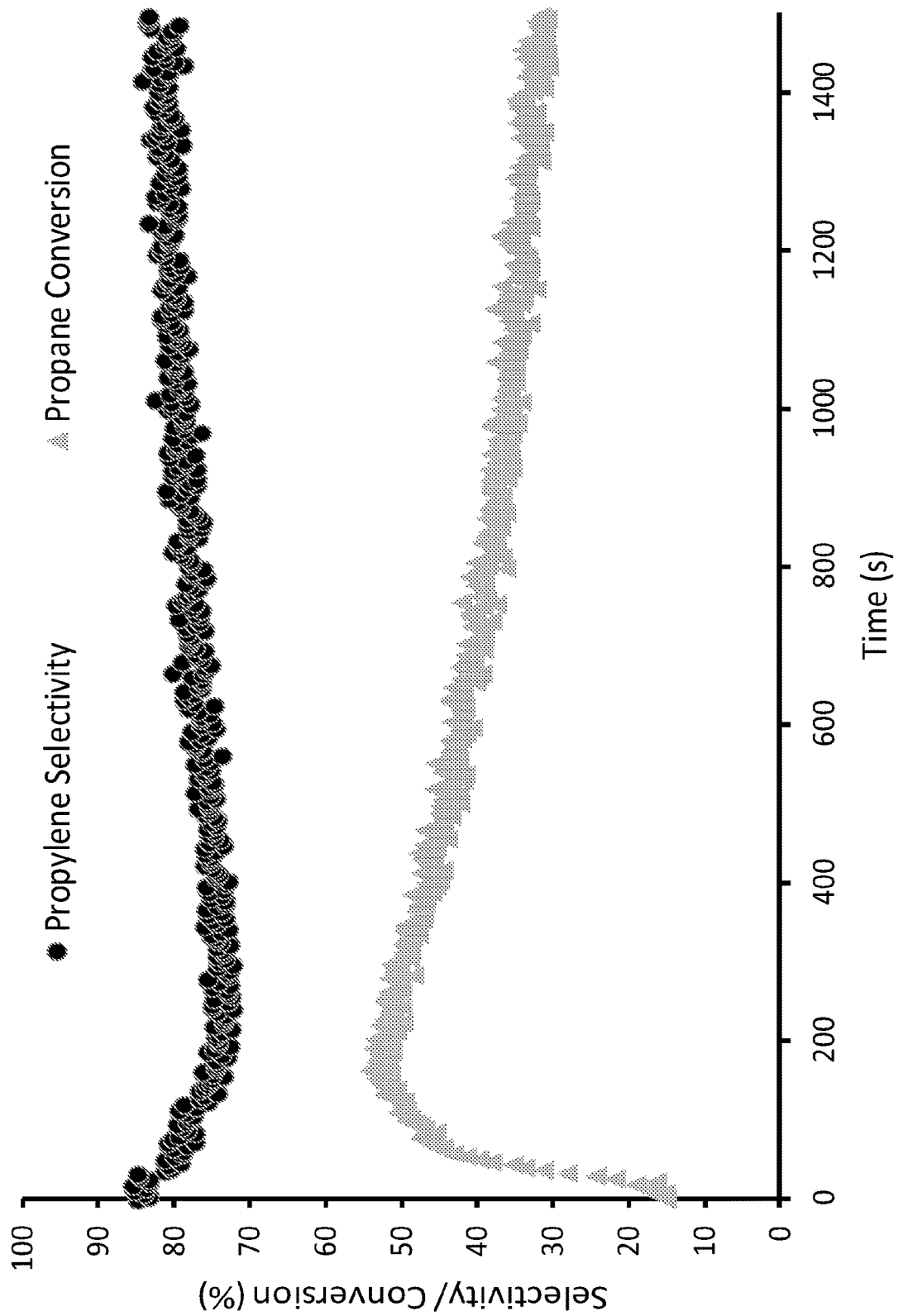
FIG. 10 is a graph showing experimental data for propane conversion and propylene selectivity values over time for an oxidative dehydrogenation reaction including propane, $H_2S$, and $Fe_{0.89}S+SiO_2$ at 600° C.
Figure 11:
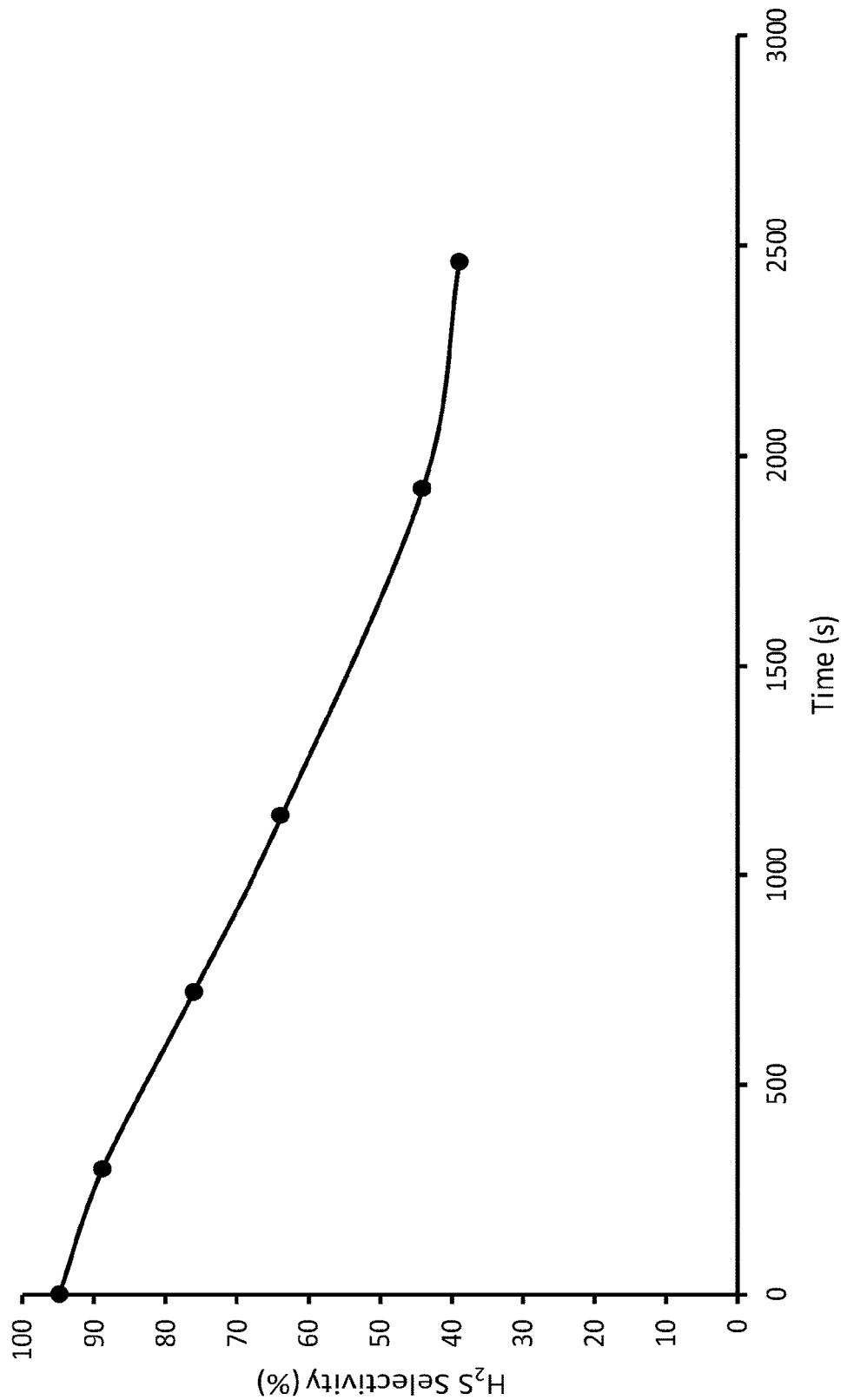
FIG. 11 is a graph showing experimental data for $H_2S$ conversion over time for the sulfidation reaction of FeS to form $Fe_{0.89}S$ at 850° C.

An example first reactor was operated at 600° C. with a propane space velocity of 60 ml/g·hr and $Fe_{0.89}S+SiO_2$ metal sulfide particles (SiO₂ present in the particles at 20 wt %). An example second reactor was operated at 800° C. with an H₂S space velocity of 15 ml/g·hr. The instruments and methodology used are similar to Example A. Results for this example system are shown in FIG. 10 and FIG. 11. FIG. 10 shows data for the first reactor, and FIG. 11 shows an H₂S sulfidation reaction of FeS to $Fe_{0.89}S$.

It appears that the added SiO₂, which played the role of a support, improved the surface area and the dispersion of active sites. The lower temperature and lower space velocity in the first reactor (compared to the experimental example above), appears to improve the overall selectivity and conversion of the system. The highest yield for propylene with this system is 39%, which the sulfidation reaction showing a similar trend as compared to the example above. The volcano trend of the yield depicts a strong dependence of the performance parameters with sulfur vacancies in the solid lattice. This provides insight into a mechanism of the first reactor (where the oxidative dehydrogenation occurs), which can be leveraged to synthesize sulfides that yield higher propylene selectivity.

C. Exemplary Fe—S System at Various Conditions

Following the example depicted in FIG. 8 and FIG. 9, several configurations of the $MS_x$-$MS_{x-1}$ pair could be envisioned. In this example, thermodynamic studies using FactSage 7.3 were done on Fe—S system to validate regenerability across a temperature range of 200° C.-1000° C. for both the reactors. 1 mol of Fe was sulfidized using 10 mols of H₂S at a given temperature and the subsequent formed metal sulfide was reacted with 1 mol of H₂ to simulate system performance. Further, $MS_x$ has been dubbed as $FeS_x$ and $MS_{x-1}$ has been dubbed as $FeS_y$. In the following reactions (7)-(9), x is the sulfur present in the most sulfidized metal phase, y is sulfur present in metal sulfide post reaction with H₂, and m is the H₂S required to regenerate $FeS_y$.

Reaction (7) shows a sulfidation step to set up the calculation.

$$Fe + 10H_2S \rightarrow FeS_x + xH_2 + (10 - x)H_2S \qquad (7)$$

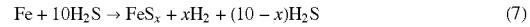

Reaction (8) shows a reaction of metal sulfide with H₂ (S—ODH).

$$FeS_x + H_2 \rightarrow FeS_y + (x - y)H_2S + (1 - (x - y))H_2 \qquad (8)$$

The reduced metal sulfide was reacted with H₂S in incremental steps till it was completely regenerated, as shown in reaction (9).

$$FeS_y + mH_2S \rightarrow FeS_x + (x - y)H_2 + (m - (x - y))H_2S \qquad (9)$$

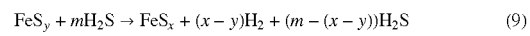

The results for this example are given below in table 1.

TABLE 1

| | Regenerability of Fe—S System | | | |
|---|---|---|---|---|
| Temperature (° C.) | Initial amount of S in sulfide (mol of S/mol of Fe) [x] | Amount of S remaining in sulfide post reaction with H₂ (mol of S/mol of Fe) [y] | Amount of S to be regenerated (mol of S/mol of Fe) | Amount of H₂S required (mol of H₂S/mol of Fe) [m] |
| 200 | 2 | 1.901 | 0.099 | 0.11 |
| 300 | 2 | 1.454 | 0.546 | 1.2 |

TABLE 1-continued

Regenerability of Fe—S System

| Temperature (° C.) | Initial amount of S in sulfide (mol of S/mol of Fe) [x] | Amount of S remaining in sulfide post reaction with $H_2$ (mol of S/mol of Fe) [y] | Amount of S to be regenerated (mol of S/mol of Fe) | Amount of $H_2S$ required (mol of $H_2S$/mol of Fe) [m] |
|---|---|---|---|---|
| 400 | 2 | 1.128 | 0.872 | 7.4 |
| 500 | 1.4 | 1.073 | 0.327 | 9 |
| 600 | 1.167 | 1.050 | 0.117 | 6 |
| 700 | 1.149 | 1.041 | 0.108 | 3.5 |
| 800 | 1.131 | 1.033 | 0.098 | 3.5 |
| 900 | 1.114 | 1.026 | 0.088 | 2 |
| 1000 | 1.098 | 1.021 | 0.077 | 1.5 |

In this experiment, it was observed that in the temperature range of 200° C.-1000° C., iron metal sulfides swing between three phases: $FeS_2$, $Fe_7S_8$ and $FeS_z$ (pyrrhotite z=1-1.25). $Fe_7S_8$ is not formed at 400° C. and above and $FeS_2$ is not formed at 600° C. and beyond. [x] and [y] values are calculated based on these phases. At lower temperatures of 200° C. and 300° C., metal sulfide swings only between $FeS_2$ and $Fe_7S_8$. As the temperature reaches 400° C. metal sulfide swings between $FeS_2$ and $FeS_z$. At 500° C., Fe is no longer sulfidized completely to $FeS_2$, and swing occurs between mixture of $FeS_2$ and $FeS_z$ and pure $FeS_z$. Beyond 500° C., swing occurs only in pyrrhotite phase with change in [z] value, for instance at 600° C. [z] value changes from 1.167 to 1.1050 as indicated from [x] and [y] values in Table 1.

It appears from Table 1 that regenerability is achieved for entire temperature spectrum under different x and y values. Regeneration requires high partial pressure of $H_2S$ and hence, higher amount of $H_2S$ is needed even if all of it does not get converted.

D. Exemplary Fe—S System with S as the Sulfur in the Sulfur Stream

In all the following experimental examples, the iron loading was kept constant at 1 mole and sulfur was used as the sulfur stream. The temperatures studied were divided into three zones based on the formation of iron sulfide phases. The temperature zones are 200-300° C., 300-650° C. and 650-900° C. In all the temperature zones, sulfur loading was varied to understand the product distribution and sulfidation extent.

1. Zone 200° C.-300° C. (T200-300)

In this temperature zone, when the sulfur loading is less than 1, it was observed that the product consists predominantly of the pyrrhotite phase. As the temperature was increased, the pyrrhotite phase decreased (FIG. 12) at a fixed sulfur loading. At these low loadings, there was no unreacted sulfur left in the solution (S-MATT) phase since it was the limiting reactant. Limiting reactant is defined with respect to a mole of stoichiometric pyrrhotite (FeS).

Figure 12:
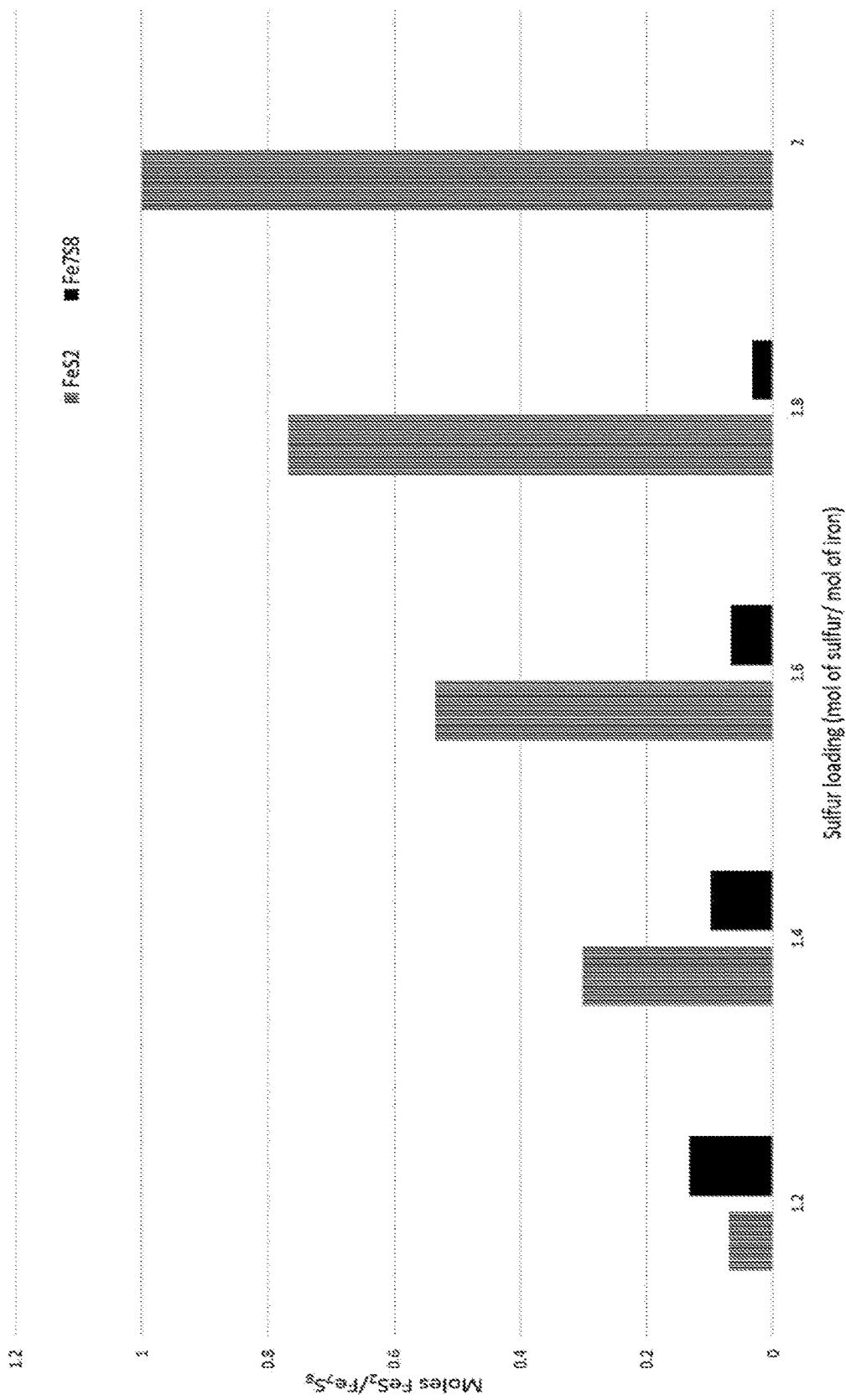
FIG. 12 is a graph showing experimental data for moles of pyrite ($FeS_2$) and $Fe_7S_8$ at sulfur loadings greater than 1.

Upon increasing the sulfur loading beyond 1 until 2, it was observed that the pyrrhotite phase decomposed completely into two phases of constant molar quantities of pyrite ($FeS_2$) and $Fe_7S_8$ without any unreacted sulfur across the entire temperature range. However, it is worth noting that with an increased sulfur loading (from 1 towards 2), the molar quantities of pyrite increased and pyrrhotite decreased across the entire temperature range as illustrated in FIG. 12. This suggests a higher sulfide product (pyrite) is favored over $Fe_7S_8$ on increasing temperature when the sulfur is in excess with respect to iron.

Upon further increasing the sulfur loading beyond 2, it was observed the pyrrhotite fully decomposed into pyrite and the excess unreacted sulfur was left in the solution (MATT) phase. There was also no formation of pyrrhotite or $Fe_7S_8$ phase at these sulfur loadings. The trend is consistent across the entire temperature range.

2. Zone 350° C.-650° C. (T350-650)

Figure 13:
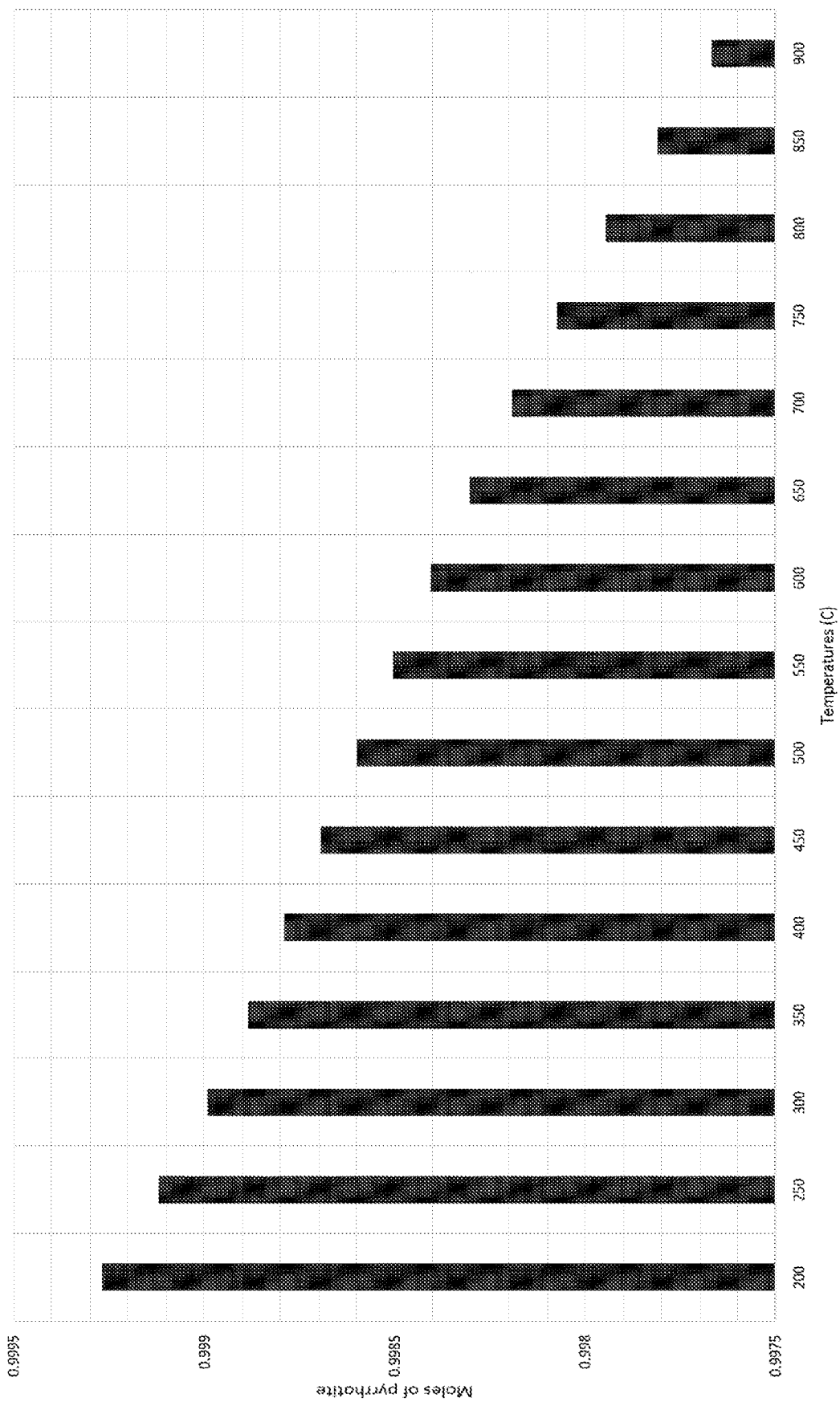
FIG. 13 is a graph showing experimental data for moles of pyrrhotite phase across temperatures 200-900° C. for sulfur loading less than 1.

In this temperature zone, when the sulfur loading is less than 1, the trends are similar to the T200-300 zone's sulfur loading <1. The product consisted of only pyrrhotite which decreased as the temperature is increased from 350° C. to 650° C. illustrated in FIG. 13.

Figure 14:
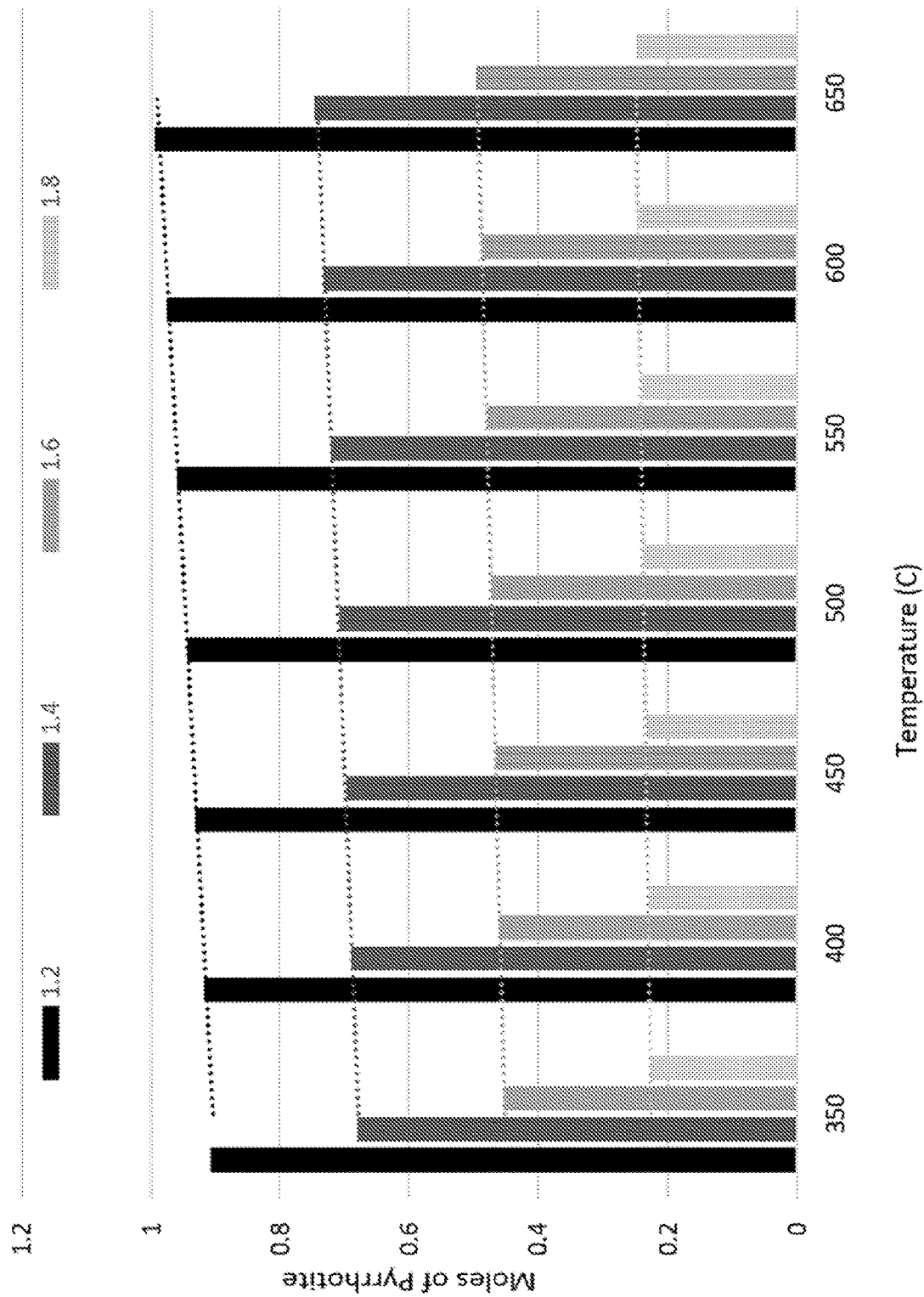
FIG. 14 is a graph showing experimental data for moles of pyrrhotite and trendlines for sulfur loadings 1-2 in the T350-650 zone.
Figure 15:
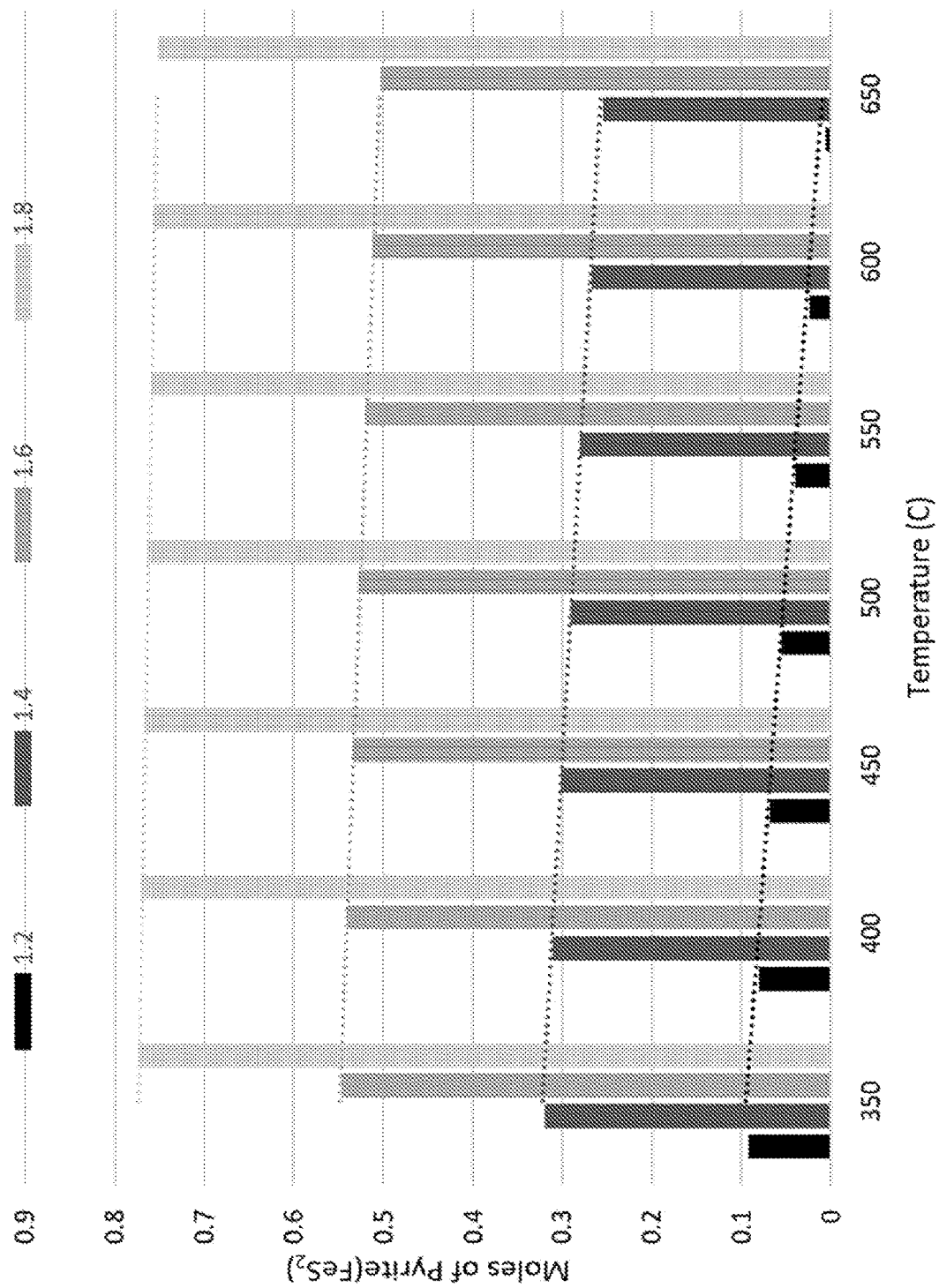
FIG. 15 is a graph showing experimental data for moles of pyrite ($FeS_2$) and trendlines for sulfur loadings 1-2 in the T350-650 zone.

When the sulfur loading is increased beyond 1 till 2, the product consisted of two phases here i.e. pyrrhotite and pyrite ($FeS_2$). There is no formation of $Fe_7S_8$ in this zone unlike previous case. The molar quantities of pyrrhotite increased while the pyrite decreased as illustrated in FIG. 14 which is attributed to the pyrite decomposition into pyrrhotite phase upon increasing the temperature. It is worth noting that in this temperature zone, for the sulfur loadings of 1 to 1.5 the dominant phase is pyrrhotite while from 1.5 to 2 it is pyrite as shown in FIG. 14. In addition, the pyrite decreases and pyrrhotite increases for sulfur loadings (1-2) with increase in temperature. This is illustrated through the trendlines in the FIG. 15.

For sulfur loadings beyond 2, no pyrrhotite is observed furthermore across the entire zone. The products obtained at excessive sulfur is a mole of pyrite and the excess unreacted sulfur in found in the solution (S-MATT) phase till 450° C. While beyond 450° C. the unreacted sulfur is present in the gas phase in the form of $S_2$ since the temperature is well beyond the boiling point of sulfur.

3. Zone 700° C.-900° C. (T700-900)

In this temperature zone, the only phase is pyrrhottite across all ranges of sulfur loading. Herein too the pyrrhottite phase decreased with increasing the temperature up until sulfur loading equals 1. For sulfur loadings beyond 1, the product consists of 1 mole of pyrrhotite and the excess unreacted sulfur is found in the gaseous phase in form of $S_2$.

4. Zone 950° C.-1000° C. (T950-1000)

In this temperature range, to avoid the MATT phase, the sulfur loading was kept at excess with respect to iron (>1). The pyrrhotite phase was formed and any unreacted sulfur was found in the gas phase in form of $S_2$.

5. Extent of Sulfidation

Figure 16:
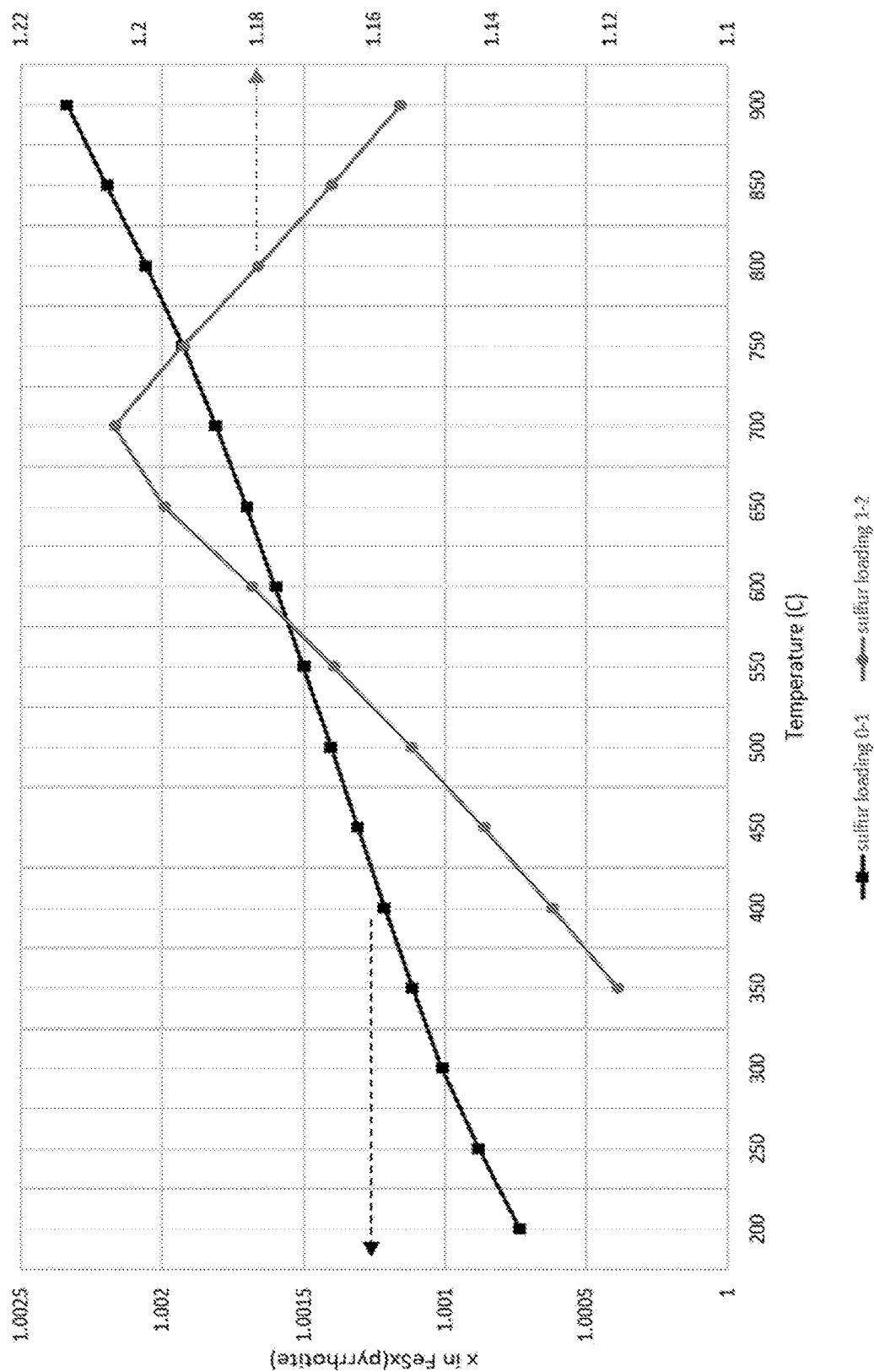
FIG. 16 is a graph showing experimental data for pyrrhotite sulfidation extent for sulfur loading 0-1 and 1-2 across temperatures 200° C.-900° C.

The sulfidation extent is measured in the pyrrhotite phase across the entire temperature range (200° C.-900° C.). It was observed that the sulfidation increased with an increase of the temperature for sulfur loadings up till 1 while the sulfidation extent is peaked at 700° C. for sulfur loadings beyond 1. This is shown in FIG. 16.

E. Experimental Example with Mixed Metal Sulfides

Figure 17:
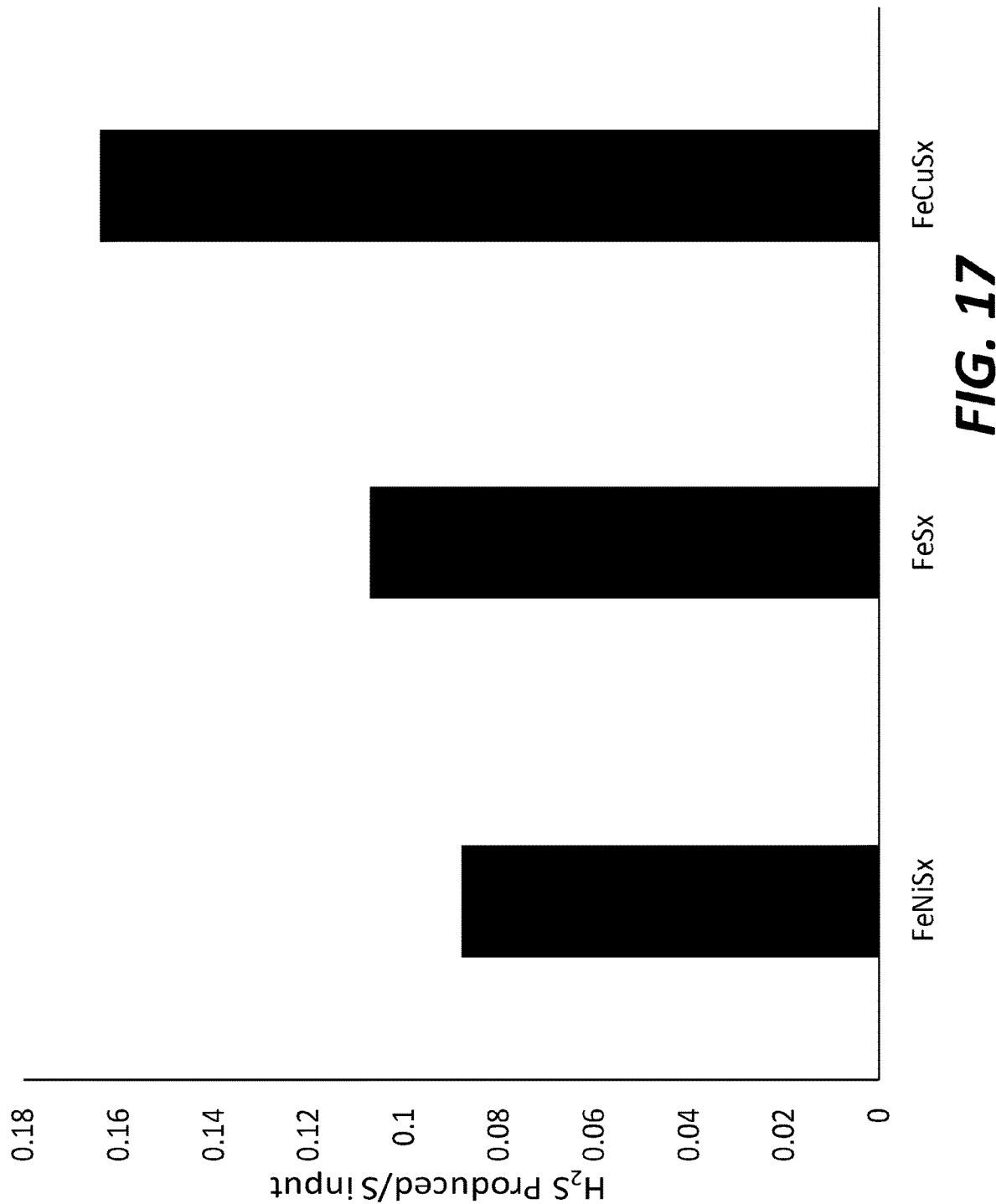
FIG. 17 is a graph showing experimental data for $H_2S$ generation capacity for different metal sulfides.

In this example, thermodynamic analysis using FactSage 7.3 was done on Fe—Ni—S and Fe—Cu—S system to determine improvement over Fe—S system. 1 mol of Fe along with 1 mol of Ni/Cu was sulfidized using 10 mols of $H_2S$ at 600° C. The formed bimetallic sulfide was reacted with 1 mol of $H_2$ at 600° C. The reactions were similar to those given in Fe—S section. Comparison based on $H_2S$ generation for different metal sulfides is depicted in FIG. 17. $H_2S$ generation is normalized with respect to sulfur present in metal sulfide.

Figure 18:
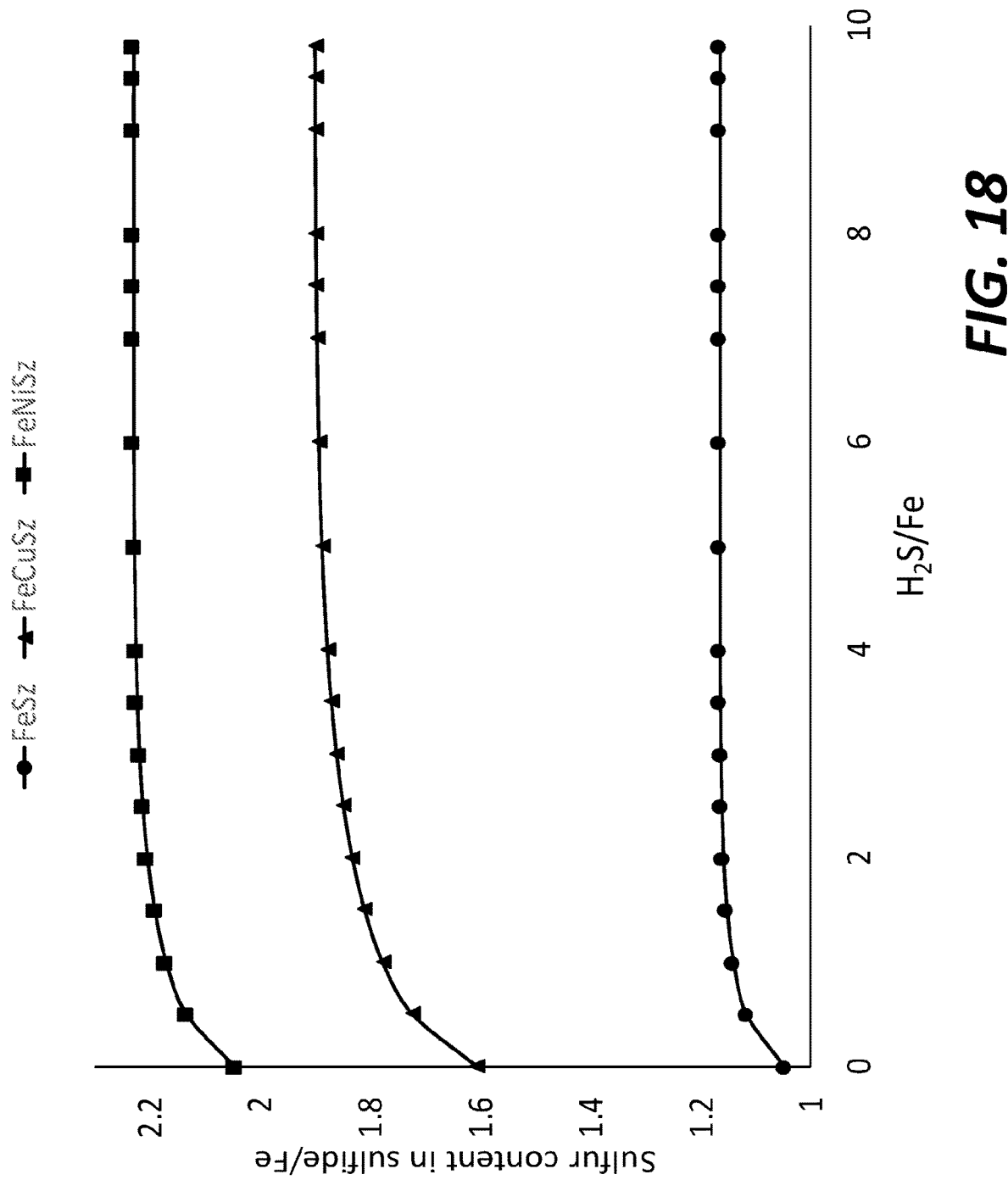
FIG. 18 is a graph showing experimental data for regenerability with $H_2S$ for different metal sulfides.

Fe—Cu—S system shows a 53% improvement in $H_2S$ formation over an Fe—S system. This means that Fe—Cu—S can push the equilibrium of alkane dehydrogenation using less amount of material. To confirm the regenerability of these bimetallic sulfides, sulfides post $H_2$ reaction were reacted with incremental amounts of $H_2S$. As an amount of Fe remains constant, $H_2S$ addition and sulfur content was normalized based on Fe to keep consistent with Fe—S single sulfide system. Both the Fe—Cu—S and Fe—Ni—S sulfides show complete regenerability at 600° C. as indicated by FIG. 18.

Like the pyrrhotite phase of Fe, bimetallic sulfides form phase of FeMSz where M is either Cu or Ni. The swing occurs between different [z] values. The change of [z] value for each sulfide can be calculated from FIG. 18 by subtracting sulfur content at zero addition of $H_2S$ with constant sulfur content achieved after addition of enough $H_2S$.

F. Experimental Example with Co—S System

Metals other than Fe can exhibit multiple sulfidation states which can be exploited for alkane dehydrogenation. In this example, thermodynamic study on another transition metal Co is performed to estimate its overall performance. Co cannot be sulfidized with $H_2S$, but it reacts with pure sulfur to form sulfides. 1 mol of Co was reacted with 10 mols of S at various temperatures. At every temperature, $CoS_2$ was obtained as the most sulfidized phase which was reacted with 1 mol of $H_2$. Based on the temperature, mixture of CoS and $CoS_2$ is obtained with generation of $H_2S$ and S.

Reaction (10) below shows sulfidation.

$$Co + 10S \rightarrow CoS_2 + 8S \quad (10)$$

Reaction (11) below shows reaction with $H_2$.

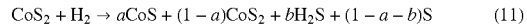

$$CoS_2 + H_2 \rightarrow aCoS + (1-a)CoS_2 + bH_2S + (1-a-b)S \quad (11)$$

Figure 19:
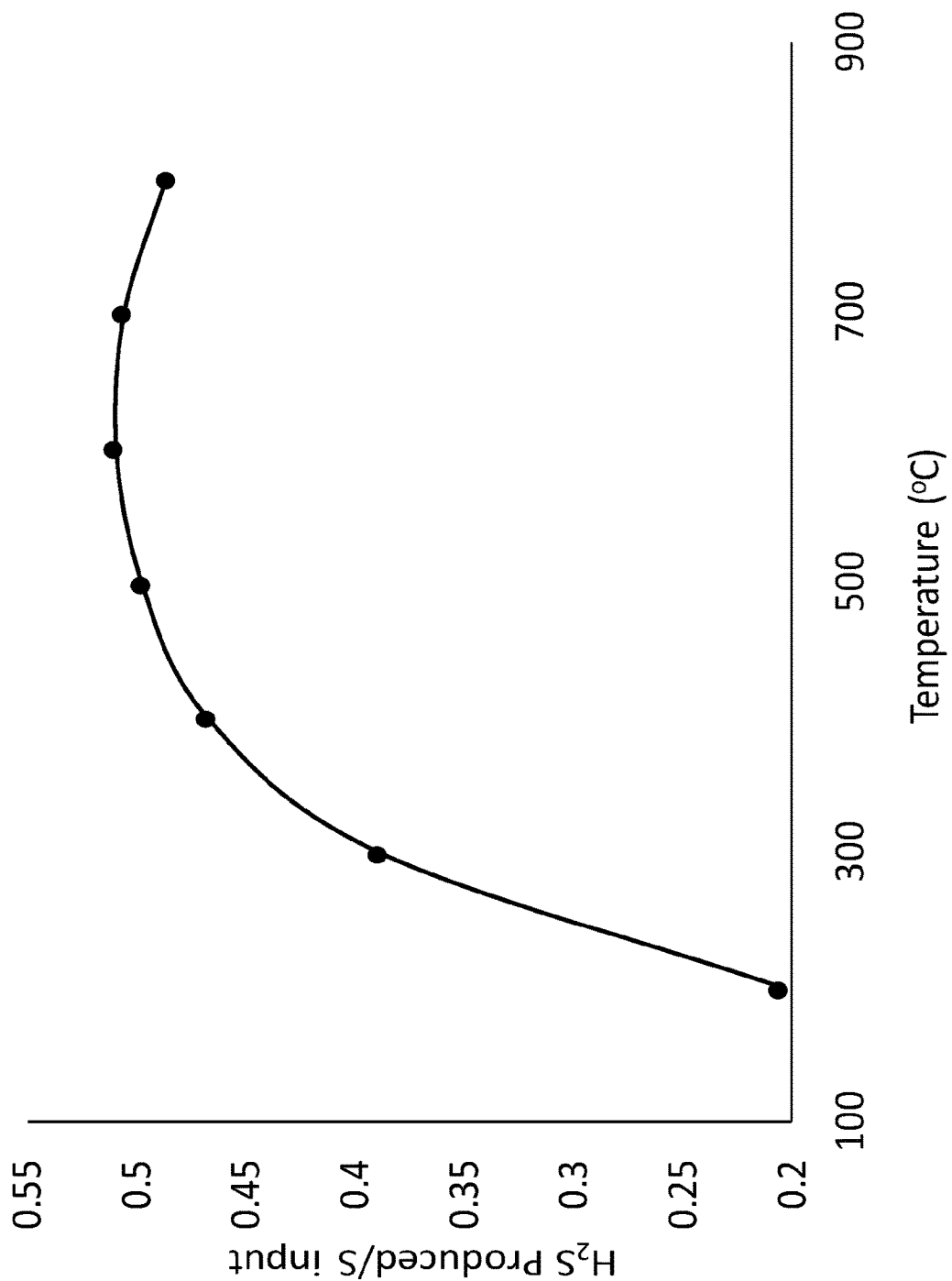
FIG. 19 is a graph showing experimental data for $H_2S$ generation capacity of a Co—S system for different temperatures.

Results for $H_2S$ and S generation are shown in FIG. 19. At low temperatures, entire conversion of $CoS_2$ is not obtained which results in poor $H_2S$ generation. Sulfur is also emitted in very low quantities at 700° C. and 800° C.

At 600° C., Co—S system is better than Fe—S system by a factor of 3.76. This huge enhancement is possible because $CoS_2$ is very easily reduced to CoS by $H_2$. CoS can be regenerated back to $CoS_2$ using sulfur for temperature range of 200° C.-800° C. as shown in Table 2.

TABLE 2

| | Regenerability of Co—S System | | | |
|---|---|---|---|---|
| Temperature (° C.) | Initial amount of S in sulfide (mol of S/mol of Co) [x] | Amount of S remaining in sulfide post reaction with $H_2$ (mol of S/mol of Co) [y] | Amount of S to be regenerated (mol of S/mol of Co) | Amount of S required (mol of S/mol of Co) [m] |
| 200 | 2 | 1.612 | 0.388 | 0.388 |
| 300 | 2 | 1.266 | 0.734 | 0.734 |
| 400 | 2 | 1.118 | 0.882 | 0.882 |
| 500 | 2 | 1.062 | 0.938 | 0.938 |
| 600 | 2 | 1.031 | 0.969 | 0.969 |
| 700 | 2 | 1 | 1 | 1 |
| 800 | 2 | 1 | 1.1 | 1.1 |

As $CoS_2$ is always achieved as the most sulfidized phase, [x] value is always 2. [y] value is calculated based on amount of CoS and $CoS_2$ present, shown below:

$$[y] = mols \text{ of } CoS + 2*mols \text{ of } CoS_2$$

As stated above, the table clearly shows low sulfide conversion at lower temperatures. In contrast to Fe—S system, excess amount of sulfidizing agent (S) is not required to fully regenerate the sulfide.

G. Experimental Example with Pb—S System

Figure 20:
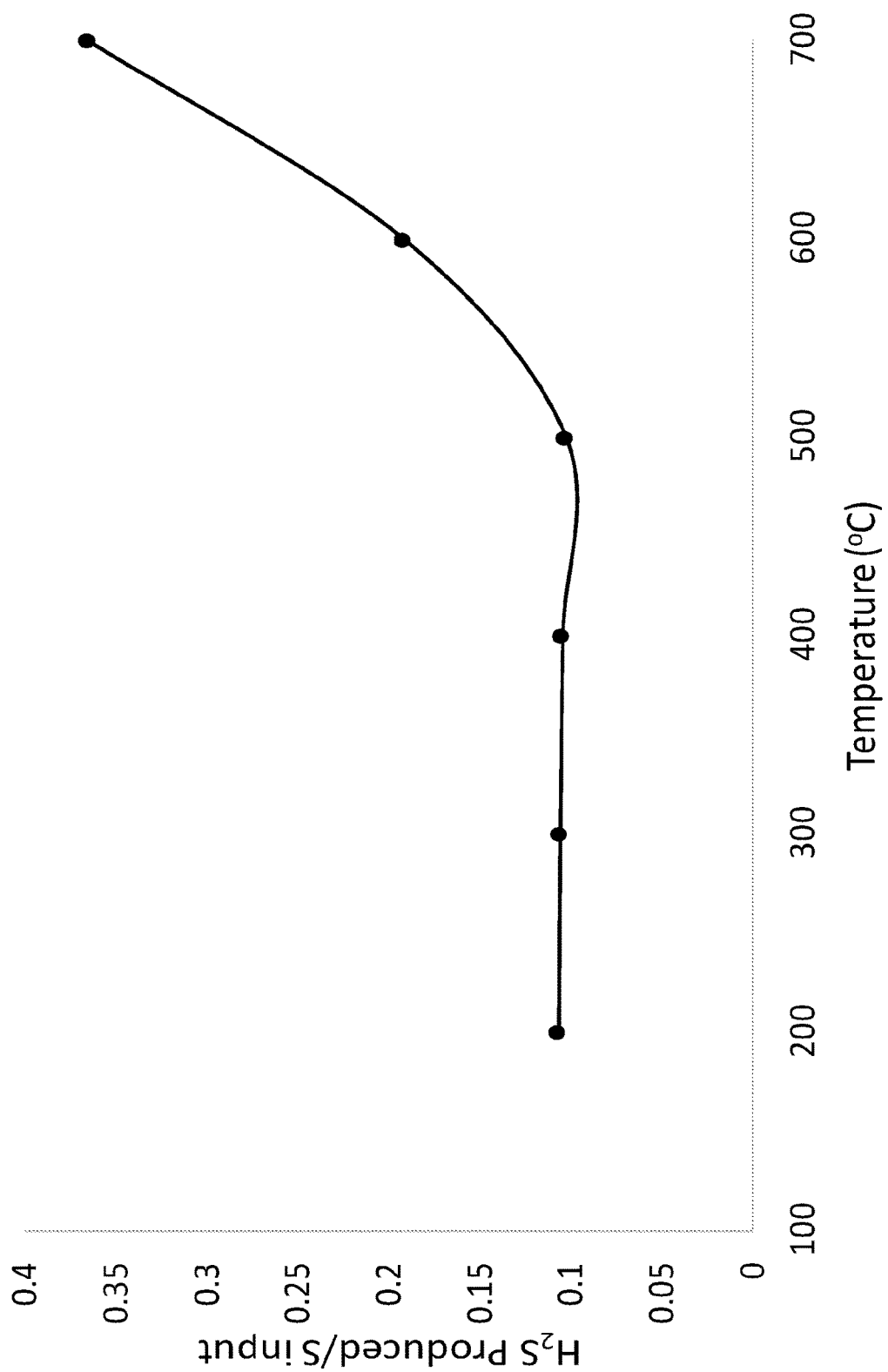
FIG. 20 is a graph showing experimental data for $H_2S$ generation capacity of a Pb—S system for different temperatures.

Similar to transition metals, even metalloids such as Pb can display multiple oxidation states. Using $H_2S$, Pb can be sulfidized only until PbS. PbS is a stable phase and does not react with $H_2$ in temperature range of 200° C.-700° C. and shows little reactivity at temperatures above 700° C. Hence, to achieve greater sulfidation, S is used to sulfidize and regenerate Pb metal sulfide. 1 mol of Pb was reacted with 10 mols of S at various temperatures. A mixture of PbS and PbSz (z>1) is obtained which is then further reacted with 1 mol of $H_2$. The reaction scheme is similar to Co. The result for $H_2S$ formation is depicted in FIG. 20.

The sulfided form of Pb tends to lose a lot of sulfur. However, as the analysis was restricted to 1 mol of $H_2$, entire potential of this metal sulfide is not captured in the above figure. Above 800° C., some Pb evaporates in form of PbS and hence temperatures only up till 700° C. are considered. PbS phase is formed only till temperatures below 400° C. while PbSz is formed in entire temperature range. The reduced metal sulfide can be regenerated using stoichiometric amount of S as seen in Table 3.

TABLE 3

Regenerability of Pb—S System

| Temperature (° C.) | Initial amount of S in sulfide (mol of S/mol of Pb) [x] | Amount of S remaining in sulfide post reaction with $H_2$ (mol of S/mol of Pb) [y] | Amount of S to be regenerated (mol of S/mol of Pb) | Amount of S required (mol of S/mol of Pb) [m] |
|---|---|---|---|---|
| 200 | 10 | 8.981 | 1.019 | 1.019 |
| 300 | 10 | 8.819 | 1.181 | 1.181 |
| 400 | 10 | 8.084 | 1.916 | 1.916 |
| 500 | 10 | 6.146 | 3.854 | 3.854 |
| 600 | 5.292 | 2.656 | 2.636 | 2.636 |
| 700 | 2.792 | 1 | 1.792 | 1.792 |

The tendency of Pb to retain S decreases as temperature increases and as almost complete conversion of $H_2$ to $H_2S$ is obtained, the $H_2S$ produced/S input parameter increases with temperature as seen in FIG. 20. However, as mentioned earlier, metal sulfides at lower temperatures are capable of processing more $H_2$, which is not studied to keep the study consistent with other metal systems. This can be seen by the difference in sulfur content between initial and reduced sulfided form (amount to be regenerated) which is being emitted as pure sulfur in this experimental example.

Unless otherwise defined, all technical and scientific terms used herein have the same meaning as commonly understood by one of ordinary skill in the art. In case of conflict, the present document, including definitions, will control. Example methods and materials are described below, although methods and materials similar or equivalent to those described herein can be used in practice or testing of the present disclosure. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated. For example, when a pressure range is described as being between ambient pressure and another pressure, a pressure that is ambient pressure is expressly contemplated.

We claim:

1. A method, comprising:
   providing a gaseous alkane input stream to a first reactor;
   providing a metal sulfide ($MS_x$) particle to the first reactor,
      whereupon the metal sulfide ($MS_x$) particle reacts with an alkane in the gaseous alkane input stream to generate an alkene, a reduced metal sulfide ($MS_{x-1}$) particle, and at least one of: hydrogen sulfide ($H_2S$) and a sulfur containing compound;
   collecting a product stream from the first reactor including the alkene, hydrogen sulfide ($H_2S$) and the sulfur containing compound;
   providing the reduced metal sulfide ($MS_{x-1}$) particle to a second reactor;
   providing a sulfur stream to the second reactor,
      whereupon the reduced metal sulfide ($MS_{x-1}$) particle reacts with sulfur in the sulfur stream to generate the metal sulfide ($MS_x$) particle and hydrogen ($H_2$); and
   collecting a second reactor output stream including hydrogen ($H_2$).

2. The method according to claim 1, wherein the alkane in the gaseous alkane input stream includes at least one $C_2$-$C_6$ alkane; and
   wherein the sulfur containing compound is one or more of: $S_2$, CS, and $CS_2$.

3. The method according to claim 1, further comprising:
   monitoring alkane content in the product stream; and
   if the alkane content differs from a predetermined target, adjusting a flow rate of the gaseous alkane input stream.

4. The method according to claim 1, wherein the sulfur stream includes hydrogen sulfide ($H_2S$).

5. The method according to claim 4, wherein the second reactor output stream further comprises hydrogen sulfide ($H_2S$), the method further comprising:
separating the hydrogen sulfide ($H_2S$) from the second reactor output stream; and
recycling the separated hydrogen sulfide ($H_2S$) to the second reactor.

6. The method according to claim 1, wherein the sulfur stream includes at least one allotrope of sulfur (S).

7. The method according to claim 1, further comprising separating the hydrogen sulfide ($H_2S$) from the product stream; and
recycling the separated hydrogen sulfide ($H_2S$) to the second reactor.

8. The method according to claim 1, further comprising:
maintaining a temperature of the first reactor to be between 200° C. and 1200° C.;
maintaining a pressure of the first reactor to be between 1 atm and 30 atm;
maintaining a temperature of the second reactor to be between 200° C. and 1000° C.; and
maintaining a pressure of the second reactor to be between 1 atm and 30 atm.

9. The method according to claim 1, wherein the sulfur stream further includes an inert carrier gas.

10. The method according to claim 1, wherein a metal (M) in the metal sulfide ($MS_x$) particle includes iron (Fe), cobalt (Co), nickel (Ni), copper (Cu), tungsten (W), lanthanum (La), cerium (Ce), titanium (Ti), zinc (Zn), cadmium (Cd), ruthenium (Ru), rhodium (Rh) or lead (Pb).

11. The method according to claim 1, wherein the metal sulfide ($MS_x$) particle includes a promotor, dopant, or support.

12. The method according to claim 11, wherein the promotor, dopant, or support is $MoS_2$, $Ce_2S_3$, MgS, $Na_2S$, $K_2O$, MgO, $SiO_2$, $Al_2O_3$, or $MgAl_2O_4$.

13. The method according to claim 1, wherein the metal sulfide ($MS_x$) particle has a size of 100 μm to 2 mm; and
wherein the metal sulfide ($MS_x$) particle has density of 1.5 g/cm³ to 6 g/cm³.

14. The method according to claim 1, wherein the metal sulfide ($MS_x$) particle includes a mesoporous support selected from: Santa Barbara Amorphous-15 silica (SBA-15), Santa Barbara Amorphous-16 silica (SBA-16), Mesoporous $Al_2O_3$, and Mesoporous $CeO_2$.

15. A method, comprising:
providing a gaseous alkane input stream to a reactor, the reactor including a metal sulfide ($MS_x$) particle,
whereupon the metal sulfide ($MS_x$) particle reacts with an alkane in the gaseous alkane input stream to generate an alkene, a reduced metal sulfide ($MS_{x-1}$) particle, and at least one of: hydrogen sulfide ($H_2S$) and at least one sulfur containing compound, the at least one sulfur containing compound being selected from: $S_2$, CS, and $CS_2$;
collecting a product stream from the reactor including the alkene and at least one of hydrogen sulfide ($H_2S$) and the at least one sulfur containing compound;
after collecting the product stream, providing an inert gas stream to the reactor;
after providing the inert gas stream to the reactor, providing a sulfur stream to the reactor,
whereupon the reduced metal sulfide ($MS_{x-1}$) particle reacts with sulfur in the sulfur stream to generate the metal sulfide ($MS_x$) particle and hydrogen ($H_2$); and
collecting a reactor output stream including hydrogen ($H_2$).

16. The method according to claim 15, further comprising:
after collecting the reactor output stream, providing the inert gas stream to the reactor,
wherein the alkane in the gaseous alkane input stream includes at least one $C_2$-$C_6$ alkane; and
wherein the sulfur stream includes hydrogen sulfide ($H_2S$).

17. The method according to claim 15, wherein the sulfur stream includes at least one allotrope of sulfur (S); and
wherein the reactor output stream includes hydrogen sulfide ($H_2S$), the method further comprising:
separating the hydrogen sulfide ($H_2S$) from the reactor output stream; and
recycling the separated hydrogen sulfide ($H_2S$) to the reactor.

18. The method according to claim 15, further comprising:
while providing the gaseous alkane input stream:
maintaining a temperature of the reactor to be between 200° C. and 1200° C.;
maintaining a pressure of the reactor to be between 1 atm and 30 atm;
while providing the sulfur stream:
maintaining a temperature of the reactor to be between 200° C. and 1000° C.; and
maintaining a pressure of the reactor to be between 1 atm and 30 atm.

19. The method according to claim 15,
wherein a metal (M) in the metal sulfide ($MS_x$) particle includes iron (Fe), cobalt (Co), nickel (Ni), copper (Cu), tungsten (W), lanthanum (La), cerium (Ce), titanium (Ti), zinc (Zn), cadmium (Cd), ruthenium (Ru), rhodium (Rh), or lead (Pb); and
wherein the metal sulfide ($MS_x$) particle includes a promotor, dopant, or support selected from $MoS_2$, $Ce_2S_3$, MgS, $Na_2S$, $K_2O$, MgO, $SiO_2$, $Al_2O_3$, or $MgAl_2O_4$.

20. The method according to claim 15, wherein the metal sulfide ($MS_x$) particle has a size of 100 μm to 2 mm;
wherein the metal sulfide ($MS_x$) particle has density of 1.5 g/cm³ to 6 g/cm³; and
wherein the metal sulfide ($MS_x$) particle includes a mesoporous support selected from: Santa Barbara Amorphous-15 silica (SBA-15), Santa Barbara Amorphous-16 silica (SBA-16), Mesoporous $Al_2O_3$, and Mesoporous $CeO_2$.

* * * * *